US010613085B2

(12) United States Patent
Taha et al.

(10) Patent No.: US 10,613,085 B2
(45) Date of Patent: Apr. 7, 2020

(54) **MONOCLONAL ANTIBODIES SPECIFIC FOR SEROGROUP X OF *N. MENINGITIDIS* AND USES THEREOF IN DIAGNOSIS**

(71) Applicant: INSTITUT PASTEUR, Paris (FR)

(72) Inventors: Muhamed-Kheir Taha, Saint Maur des Fosses (FR); Alain Agnememel, Freneuse (FR)

(73) Assignee: INSTITUT PASTEUR, Paris (FR)

( * ) Notice: Subject to any disclaimer, the term of this patent is extended or adjusted under 35 U.S.C. 154(b) by 119 days.

(21) Appl. No.: 15/580,330

(22) PCT Filed: Jun. 8, 2016

(86) PCT No.: PCT/EP2016/062994
§ 371 (c)(1),
(2) Date: Dec. 7, 2017

(87) PCT Pub. No.: WO2016/198435
PCT Pub. Date: Dec. 15, 2016

(65) Prior Publication Data
US 2018/0180610 A1 Jun. 28, 2018

(30) Foreign Application Priority Data
Jun. 9, 2015 (EP) .................................... 15305877

(51) Int. Cl.
*G01N 33/569* (2006.01)
*C07K 16/12* (2006.01)

(52) U.S. Cl.
CPC .... *G01N 33/56911* (2013.01); *C07K 16/1217* (2013.01); *C07K 2317/14* (2013.01); *C07K 2317/33* (2013.01); *C07K 2317/565* (2013.01); *G01N 2333/22* (2013.01); *G01N 2400/10* (2013.01); *G01N 2469/10* (2013.01); *G01N 2800/26* (2013.01)

(58) Field of Classification Search
None
See application file for complete search history.

(56) References Cited

U.S. PATENT DOCUMENTS

2017/0334975 A1 11/2017 Taha et al.

OTHER PUBLICATIONS

Reyes (Biologicals 42:312-315, 2014).*
O'Ryan et al., "A Multi-Component Meningococcal Serogroup B Vaccine (4CMenB): The Clinical Development Program," Drugs, 74:15-30 (2014).
Hong et al., "Could the multicomponent meningococcal serogroup B vaccine (4CMenB) control Neisseria meningitidis capsular group X outbreaks in Africa": Vaccine, 31:1113-1116 (2013).
Boisier et al., "Meningococcal Meningitis: Unprecedented Incidence of Serogroup X—Related Cases in 2006 in Niger," Clin Infect Dis., 44:657-663 (2007).
Taha et al., "Neisseria meningitidis Serogroups W135 and A Were Equally Prevalent among Meningitis Cases Occurring at the End of the 2001 Epidemics in Burkina Faso and Niger," J Clin Microbiol., 40:1083-1084 (2002).
Collard et al., "Epidemiological changes in meningococcal meningitis in Niger from 2008 to 2011 and the impact of vaccination," BMC Infect Dis., 13:576 (2013).
Terrade et al., "Laboratory evaluation of a rapid diagnostic test for Neisseria meningitidis serogroup A.," Trans R Soc Trop Med Hyg, 107: 460-461 (2013).
Chanteau S et al., "Scaling up of PCR-based surveillance of bacterial meningitis in the African meningitis belt: indisputable benefits of multiplex PCR assay in Niger," Trans R Soc Trop Med Hyg. 100: 677-680 (2006).
Chanteau et al., "New rapid diagnostic tests for Neisseria meningitidis serogroups A, W135, C, and Y," PLoS Med., 3: e337 (2006).
European Centre for Disease Prevention and Control. 2013. Annual Epidemiological Report 2012. Reporting on 2010 surveillance data and 2011 epidemic intelligence data. Stockholm: ECDC. Extract p. 168-172 +i) -> xvi).
Micoli F et al., "Development of a glycoconjugate vaccine to prevent meningitis in Africa caused by meningococcal serogroup X," Proc Natl Acad Sci U S A. 110: 19077-19082 (2013).
Ballard et al., "Comparison of three latex agglutination kits and counterimmunoelectrophoresis for the detection of bacterial antigens in a pediatric population," Pediatr Infect Dis J., 6:630-634 (1987).
Nato et al., "Production of Polyclonal and Monoclonal Antibodies against Group A, B, and C Capsular Polysaccharides of Neisseria meningitidis and Preparation of Latex Reagents," J Clin Microbiol., 29:1447-1452 (1991).
Xie et al., "Characterization of size, structure and purity of serogroup X Neisseria meningitidis polysaccharide, and development of an assay for quantification of human antibodies," Vaccine., 30:5812-5823 (2012).
Chanteau et al., "Development and testing of a rapid diagnostic test for bubonic and pneumonic plague," Lancet., 361:211-216 (2003).
Rissin et al., "Single-molecule enzyme-linked immunosorbent assay detects serum proteins at subfemtomolat concentrations," Nat. Biotechnol. 28:595-600 (2010).

(Continued)

*Primary Examiner* — Patricia Duffy
(74) *Attorney, Agent, or Firm* — Arrigo, Lee, Guttman & Mouta-Bellum LLP

(57) ABSTRACT

The present invention is directed to monoclonal antibodies and antigen-binding portions thereof, specific for the capsular polysaccharides of *Neisseria meningitidis* serogroup X (NmX), wherein said antibodies or portions thereof are characterized by the sequences of the 6 CDR of the variable regions of the heavy and light chains. These antibodies are suitable for in vitro detection of *Neisseria meningitidis* serogroup X especially in a biological sample without purification of the capsular polysaccharides. The invention also concerns said monoclonal antibodiesor adequate portions thereofin different diagnostic tests and methods, in order to detect NmX. The invention discloses also a rapid diagnostic test for detecting NmX in a biological fluid.

Figure 1:
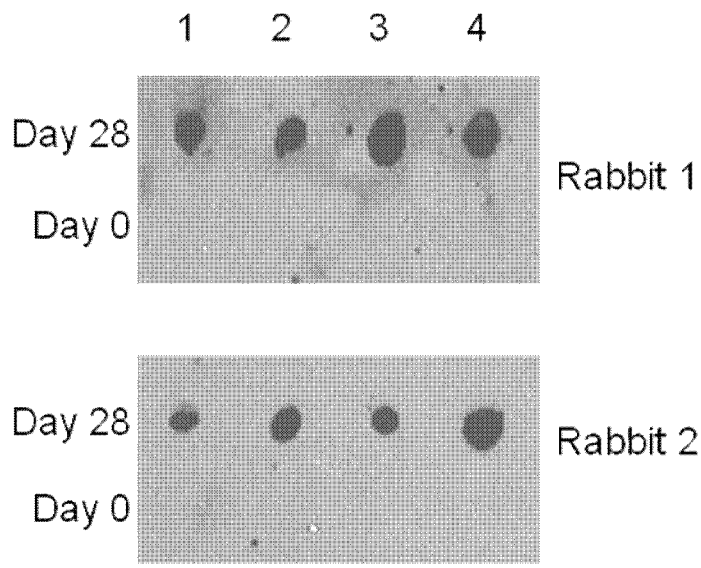

17 Claims, 6 Drawing Sheets
Specification includes a Sequence Listing.

(56) References Cited

OTHER PUBLICATIONS

Agnememel et al., "Development and evaluation of a dipstick diagnostic test for Neisseria meningitidis serogroup X" Journal of Clinical Microbiology, American Society for microbiology, United States, vol. 53, n° C. 2, 449-454 (2015).
Reyes et al., "A novel monoclonal antibody to Neisseria meningitidis serogroup X capsular polysaccharide and its potential use in quantitation of meningococcal vaccines" Biologicals, 42(6):312-315 (2014).
Scaviner et al., "Protein Displays of the Human Immunoglobulin Heavy, Kappa and Lambda Variable and Joining Regions," Exp. Clin. Immunogenet., 16:234-240 (1999).
Kaas et al., "IMGT Colliers de Perles: Standardized Sequence-Structure Representations of the IgSF and MhcSF Superfamily Domains," Current Bioinformatics, 2:21-30 (2007).
Agnememel et al., "Characterization and immunogenicity of Neisseria meningitidis serogroup X capsular polysaccharide, a step forward for rapid diagnostic test" Abstract book meeting, 2013, 1-114.
Payne et al., "Clinical laboratory applications of monoclonal antibodies" Clinical Microbiology Reviews, 313-329 (1988).
Ala'adeen D A A et al, The meningococcal transferrin-binding proteins 1 and 2 are both surface exposed and generate bactericidal antibodies capable of killing homologous and heterolouous strains, Vaccine, vol. 14, No. 1, 1996, pp. 49-53.
Clezardin P et al, Tandem Purification of IgM Monocolonal Antibodies From Mouse Ascites Fluids by Anion-Excange and Gel Fast Protein Liquid Chromatography, Chrom. 18 261, 1986, pp. 425-433.
Ritter M A, "Polyclonal and Monoclonal Antibodies," Methods in Molecular Medicine, vol. 40: Diagnostic and Therapeutic Antibodies, Aug. 1, 2000.
Angela M. C. Rose et al "Meningitis Dipstick Rapid Test : Evaluating Diagnostic Performance during an Urban Neisseria meningitidis Serogroup A Outbreak, Burkina Faso, 2007" PLOS One, vol. 5, n°C.6, 2010.
Alain Agnememel et al : "Characterization and immunogenicity of Neisseria meningitides serogroup X capsular polysaccharide a step forward for rapid diagnostic test", Abstract book EMGM meeting 2013, p. 33.
AFSSAPS Report, Nov. 25, 2009, by Dr Natacha Charler-Bret.
David R. Bundle et al : "Studies on the Group-specific Polysaccharide of Neisseria meningitidis Serogroup X and an Improved Procedure for its Isolation", The Journal of Biological Chemistry, vol. 249, N° 15, 1974, 4797-4801.
A. van der Ende et al : "Comparison of Commercial Diagnostic Tests for Identification of Serogroup Antigens of Neisseria meningitides", Journal of Clinical Microbiology, 1995, 3326-3327.
Communication Pursuant to Article 94(3) EPC, European Application No. 15798013.7, dated Oct. 9, 2018.

* cited by examiner

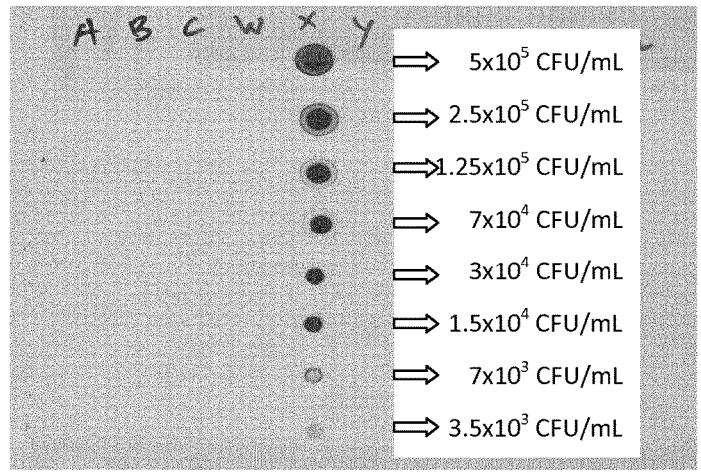

FIG.7

```
K1_H  5'  IGLVAPSQSMYITCTVSGFSLTSYGVHWVRQPPGKGLEWLGVIWAGGSTNYNSALMSRLS  60
K7_H      IGLVAPSQSLSITCTVSGFSLTSYGVHWVRQPPGKGLEWLGVIWAGGSTNYNSALMSRLS  60
          ********  **************************************************

K1_H      ISKDNSKSQVFLKMNSLQTDDTAMYYCARALLRGAMDYWGQGTSVTVSSESQSFPNVFPL--  120
K7_H      ISKDNSKSQVFLKMNSLQTDDTAMYYCARALLRGAMDYWGQGTSVTVSSESQSFPNVFPL--  120
          ************************************************************

KI_L  5'  LSLPVSLGDQASISCRSSQSLVHSNGNTYLHWYLQKPGQSPKLLIYKVSNRFSGVPDRFS  60
K7_L      LSLPVSLGDQASISCRSSQSLVHSNGNTYLHWYLQKPGQSPKLLIYKVSNRFSGVPDRFS  60
          ***********************************************************

KI_L      GSGSGTDFTLKISRVEAEDLGVYFCSQSTHVPPTFGGGTKLEIKRADAAPTVSIFPPSSE--  120
K7_L      GSGSGTDFTLKISRVEAEDLGVYFCSQSTHVPPTFGGGTKLEIKRADAAPTVSIFPPSSE--  120
          ************************************************************
```

FIG.8

MONOCLONAL ANTIBODIES SPECIFIC FOR SEROGROUP X OF *N. MENINGITIDIS* AND USES THEREOF IN DIAGNOSIS

The present invention is in the domain of bacterial detection, specifically detection of *Neisseria meningitidis* (Nm) serogroup X and diagnostic kits allowing the detection of said serogroup, preferably in a biological sample.

*Neisseria meningitidis* (Nm) is an exclusively human capsulated bacterium that can provoke severe invasive infections such as meningitis and septicaemia (1). Meningococcal disease is still a major public health concern due to potential epidemic spread. While the disease occurs sporadically in Europe and North America, it is responsible for major recurrent epidemics in Africa, occurring generally in small clusters, with seasonal variation.

The largest incidence of meningococcal disease occurs in an area of sub-Saharan Africa known as the African meningitis belt (2), which stretches from Senegal in the west to Ethiopia in the east. During the dry season, dust winds, cold nights and upper respiratory tract infections combine to damage the nasopharyngeal mucosa, increasing the risk of meningococcal disease. Moreover, transmission of *N. meningitidis* may be facilitated by overcrowded housing and by large population displacements at the regional level due to pilgrimages and traditional markets. This combination of factors explains the large epidemics which occur during the dry season in the meningitis belt.

The bacterial capsular polysaccharide determines the 12 Nm serogroups currently described. Six serogroups (A, B, C, Y, W and X) are responsible for the vast majority of cases of meningococcal disease worldwide. However, they differ in their global frequencies and geographical distribution (3). This distribution impacts on vaccination strategies, which for the most part involve the established polysaccharide-based vaccines against serogroups A, C, Y and W. In addition, an innovative recombinant protein-based vaccine was recently licensed in Europe and Australia against meningococci of serogroup B (4). This multicomponent vaccine targets conserved proteins among meningococci regardless of their serogroup. Therefore, it has the potential to cover non-serogroup B isolates such as those of serogroup X (5). In the meningitis belt, *N. meningitidis* serogroup A (NmA) predominated prior to the introduction of the NmA polysaccharide-protein conjugate vaccine (MenAfriVac™) (6), while other serogroups, mainly serogroups W (NmW) and X (NmX), were also detected and still are. Of particular concern, outbreaks due to isolates of NmW and NmX were recently reported in Africa (7-9). Surveillance of the distribution of meningococcal serogroups is therefore important and its comprehensiveness will benefit from diagnosis tools that can be widely used at the bedside.

Indeed, the WHO strategy for controlling epidemic meningococcal disease, especially in the *meningitidis* belt is based on an early and accurate detection and rapid implementation of mass vaccination using vaccines against the appropriate serogroups. It is thus imperative to rapidly and reliably identify the serogroups involved in meningococcal infection, in order to select the most appropriate vaccine. This appropriate vaccination allows the control of the epidemic clonal spread and thus plays an essential role in limiting the incidence of the outbreaks. An error in the detection of the serogroup impairs and delays the efficacy of this control, emphasizing the importance of the sensitivity and specificity of the serogroup determination.

Two strategies are generally applied for detecting the *N. meningitidis* serogroups involved in a meningococcal infection. The first one is the classic culture with subsequent identification of serogroups using specific antisera. The second one is based on the direct detection of the serogroups in a biological sample from the diagnosed or affected individuals.

With respect to culture isolation, this technique, with strain serogrouping by immune specific antisera, is generally considered as one of the reference standards for identification of *N. meningitidis* serogroups, since this technique is generally considered as specific, but this technique is poorly adapted to field detection, especially in Africa, where laboratory facilities can be at some distance away from the area of sample collection, necessitating special transport and preservation conditions of the samples. The time taken for sample transfer as well as the hot, dusty conditions experienced during the *meningitidis* season can lead to high levels of sample contamination. Moreover, the early antibiotherapy recommended in case of a suspected infection diminishes the efficacy of this method. It has also been reported that the specific antisera, used for serogroup identification on strains, do not accurately detect serogroup X and/or give rise to false-positive scores (Afssaps report, 25 Nov. 2009, by Dr Natacha Charler-Bret).

Regarding the non-culture tests, they rely either on immune detection or on genetic detection. Genetic detection is carried out generally by multiplex PCR method. This method is highly specific and very sensitive. It takes however several hours before a result can be obtained. Moreover, this technique is expensive and requires well-equipped laboratories with specialized technicians; this method is thus not well adapted to field conditions.

The non-culture tests based on immune detection of *N. meningitidis* were until recently essentially limited to latex agglutination tests on cerebrospinal fluid (CSF), such as Pastorex (Bio-Rad Laboratories, Inc.). Latex agglutination tests are rapid, sensitive, less labour-intensive and much less expensive than routine culture tests. These tests are however not routinely recommended, because they do not differentiate between serogroups W (previously known as W135) and Y, do not detect serogroup X, and their performance under field conditions lacking basic laboratory equipment is presumably weak. Furthermore, these kits require cold storage and well-trained technicians for the read-out and they may result in a few indeterminates, false negatives, and false-positives.

An immunochromatography dipstick rapid diagnostic test (RDT) for the identification of *N. meningitidis* serogroups A, C, Y and W (10-11) has been developed and validated. This major achievement was a first step to improve bedside diagnosis of meningococcal infection in Niger, a country within the meningitis belt (10,12). This test however does not identify serogroup X.

While NmX is still rare in Europe (13), its increasing importance in the meningitis belt favours the licensing of an efficient diagnosis device against NmX infection as well as ongoing studies toward a NmX polysaccharide-based vaccine (14).

Recently, the present inventors have developed an immunochromatography dipstick rapid diagnostic test (RDT) for the identification of *N. meningitidis* serogroup X (EP14 306 832.8). This test is based on polyclonal antibodies, which are highly specific for the capsular polysaccharides of *Neisseria meningitidis* serogroup X and can detect these polysaccharides with an improved sensitivity. These antibodies are inter alia highly suitable for detecting this serogroup in body fluid, without culture, allowing a rapid diagnostic test (RDT) for the detection of NmX isolates. Such a RDT can be used for the diagnosis and surveillance of meningococcal *meningitidis* in the *meningitidis* belt. It is rapid, does not require well-equipped laboratories with specialized technicians, and also is not expensive, and thus can advantageously be used in field conditions.

This test however uses polyclonal antibodies obtained by immunizing an animal, and not monoclonal antibodies, the production of which can be obtained indefinitely and identically from a hybridoma.

Reyes et al (31) discloses a monoclonal antibody against NmX polysaccharides. This antibody was however raised against purified polysaccharides, conjugated to tetanus toxoid; neither its reactivity nor its cross-reactivity with other serogroups was tested on whole bacteria; moreover, its cross-reactivity with serogroup B is unknown. The suitability of this antibody to detect specifically group X of *N. meningitidis* bacteria, especially in a diagnostic test, is entirely unknown and cannot be predicted.

There is therefore a need to provide a rapid diagnostic test for NmX, with limited variation in performance from batch-to-batch and providing reproducible results; there is also a need to provide a more reproducible and industry grade rapid diagnostic test to complete the set of bedside diagnostic tools for the detection of meningococcal meningitis. There is thus a need to provide an antibody capable of detecting group X of *N. meningitidis* with high sensitivity and specificity, obtainable in a reproducible manner, allowing standardized rapid diagnostic test, which remains stable over time with minimal variation in performance.

The present inventors have unexpectedly obtained and characterized two *N. meningitidis* serogroup X monoclonal antibodies, recognizing both purified capsular polysaccharides of *N. meningitidis* serogroup X and *N. meningitidis* serogroup X isolates. Using these monoclonal antibodies, the inventors have obtained for the first time an immunological test to detect *N. meningitidis* serogroup X bacteria with monoclonal antibodies, and have demonstrated that these antibodies can be used in rapid diagnostic tests, as a substitute for the polyclonal antibodies described in the experimental section, and in EP14 306 832.8.

According to a first aspect, the present invention is thus directed to a monoclonal antibody or an antigen-binding portion thereof, which is specific for the capsular polysaccharides of *Neisseria meningitidis* serogroup X (NmX).

In nature, antibodies are glycoprotein molecules produced by B lymphocytes. Generally speaking, antibodies bind antigens with a high degree of specificity, and can be subdivided on the basis of physical and functional properties into five classes (or isotypes), designated IgG, IgM, IgA, IgD and IgE. These different types of antibodies share a common basic structural unit which has a molecular weight of approximately 150,000 Daltons (150 kDa) and is composed of two identical heavy (H) polypeptide chains and two identical light (L) chains, covalently bonded via interchain disulfide (S-S) linkages between cysteine residues. The antibodies of the invention also have this structure.

Five different H chains exist in nature, designated alpha (α), gamma (γ), delta (δ), epsilon (ε), and mu (μ), which differ from each other in amino acid sequence. The isotype of a given antibody (i.e. whether it belongs to the IgA, IgG, IgD, IgE, or IgM class) is determined by the H chain of the antibody in question, the alpha H chain defining the IgA isotype, the gamma H chain defining the IgG isotype etc. . . . Within the IgG class there are four sub-classes designated IgG1 to IgG4.

Two different light (L) chains exist in nature, designated kappa (κ) and lambda (λ), which differ from each other in amino acid sequence.

The variable region of the heavy chain and of the light chains both contain three hypervariable regions, called "complementarity-determining regions" (CDRs), designated CDR1, CDR2 and CDR3, for the heavy and for the light chains. The CDRs of the heavy and light chains have a length of about 3 to 25 amino acids and play a key role in antibody specificity.

The monoclonal antibody or portion thereof according to the invention, specifically binding to NmX capsular polysaccharides, comprises:

at least one heavy chain variable region ($V_H$) which comprises a heavy chain CDR1 (complementarity-determining region 1) set forth in SEQ ID NO: 1, a heavy chain CDR2 set forth in SEQ ID NO: 2 and a heavy chain CDR3 set forth in SEQ ID NO: 3; and a light chain variable region ($V_L$) comprising a light chain CDR1 set forth in SEQ ID NO: 4, a light chain CDR2 set forth in SEQ ID NO: 5 and a light chain CDR3 set forth in SEQ ID NO: 6.

The complementarity-determining regions according to the invention have been defined by the International Immunogenetics Information System® (www.imgt.org), using well known techniques (32, 33). The heavy chain variable region and light chain variable region are preferably associated, within the antibody or antigen-binding portion thereof according to the invention.

The antibodies of the invention may be produced by B lymphocytes, by hybridoma, by expression of the recombinant antibody in a prokaryotic or eukaryotic host cell, or by synthetic techniques such as antibody engineering from existing antibodies. They may or may not be glycosylated.

In the context of the present invention, an 'antibody fragment' or 'antibody portion' means an antigen-binding portion of the antibody, and includes variants of such portions, even if not strictly speaking fragment of an antibody, provided they are able to specifically bind the same antigen, namely NmX capsular polysaccharides. Preferred examples of antigen-binding fragments or portions according to the invention are Fab fragments; Fab' fragments; F(ab')$_2$ fragments, scFv (single chain variable fragment) and minibodies, as well as portions of antibody comprising at least a Fab' region. Antigen-binding portions of an antibody are easily determined by a skilled person.

Variants of such fragments include dimers, and trimers of the fragments, and inter-fragment fusions. Fragments of the invention may be monovalent (for example Fab fragments), bivalent (for example F(ab')$_2$ fragments) or multivalent (for example a chemical conjugate comprising a trimeric Fab fragment).

Any reference in the following to an antibody fragment or portion, or fragment according to the invention, or antigen-binding fragment/portion, are used interchangeably, to design an antigen-binding portion of the antibody of the invention, specifically binding NmX capsular polysaccharides, and comprising at least a heavy chain variable region ($V_H$) which comprises a heavy chain CDR1 (complementarity-determining region 1) set forth in SEQ ID NO: 1, a heavy chain CDR2 set forth in SEQ ID NO: 2 and a heavy chain CDR3 set forth in SEQ ID NO: 3; and an associated light chain variable region ($V_L$) comprising a light chain CDR1 set forth in SEQ ID NO: 4, a light chain CDR2 set forth in SEQ ID NO: 5 and a light chain CDR3 set forth in SEQ ID NO: 6.

The monoclonal antibodies and portions of the invention are thus characterized by the specific 6 CDR of the heavy and light chains, the amino acid sequence of which are illustrated in FIG. 8 (SEQ ID NO:1 to 6).

The amino acid sequence of the variable region of the light chain together with the variable region of the associated heavy chain form the antigen binding site of the antibody or fragment thereof, the specificity of which is determined by the 3 CDR of the heavy chain and the 3 CDR of the light chains.

The light chain of an antibody or portion thereof according to the invention is preferably a typical kappa light chain, for example a human or murine kappa light chain.

The heavy chain of an antibody or portion thereof according to the invention is preferably a mu (μ) heavy chain, or a gamma (γ) heavy chain, or a fragment of such a chain preferably comprising the whole variable region, for example a fragment as found in Fab or Fab'.

The idiotype of the monoclonal antibodies or portions thereof according to the invention is thus preferably IgG or IgM.

It is particularly preferred that the monoclonal antibodies are IgM antibodies or antigen-binding portions thereof, as defined above, specifically binding the capsular polysaccharides of N. meningitidis serogroup X, and comprising the 6 CDRs set forth in SEQ ID No 1 to 6. A monoclonal antibody according to the invention is capable of detecting the N. meningitidis serogroup X capsular polysaccharides in situ, i.e. on the bacteria, as part of the capsule, or on bacteria fragments or on blebs (outer membrane fragments released during bacterial growth) as found in biological samples. Due to the weak immunogenicity of the bacterial capsular polysaccharides, the antibodies recognizing capsular polysaccharides are indeed generally obtained by raising antibodies against purified capsular polysaccharides, conjugated to a peptidic moiety, e.g. tetanus toxoid, in order to enhance the immunogenic reaction of the host animal. The lack of immunogenicity of the bacterial capsular polysaccharides is well known especially for *Neisseria meningitidis* bacteria; moreover, capsular polysaccharides of the serogroup X appear to be even less immunogenic than polysaccharides of the other serogroups.

Contrary to the antibodies described in the prior art, the antibodies or portions thereof according to the invention are capable of specifically recognizing the NmX polysaccharide when present on the bacteria, especially as part of the capsule, or on blebs. There is thus no need for purification of the polysaccharides in order to detect NmX bacteria in a sample, when using the antibodies or portions thereof according to the invention. The antibodies or portions thereof of the invention are thus suitable for in vitro detection of *Neisseria meningitidis* serogroup X in a biological sample without purification. Monoclonal antibodies or portions thereof according to the invention are capable of recognizing both purified capsular polysaccharides of *N. meningitidis* serogroup X (cpsX) and *N. meningitidis* serogroup X isolates or fragments thereof, or blebs.

Moreover, the antibodies or fragments of the invention as defined above are capable of detecting the *N. meningitidis* serogroup X capsular polysaccharides in solution. They are indeed sufficiently sensitive to detect soluble polysaccharides characteristic of NmX. The monoclonal antibodies according to the invention, as well as their fragments as defined above, are thus suitable for the in vitro detection of *Neisseria meningitidis* serogroup X in biological fluids, without requiring any step of culture. The monoclonal antibody is thus suitable for detecting soluble antigens of NmX, especially in clinical samples, extracted from biological fluids, and in any solution comprising bacterial extracts such as blebs.

A monoclonal antibody or fragment thereof according to the invention is inter alia suitable for in vitro detection of *Neisseria meningitidis* serogroup X by immunochromatography. It has indeed been reported that some monoclonal antibodies, although considered as specific when screened by ELISA, appear to cross react with other serogroups when assessed by immunochromatography (21). The monoclonal antibody according to the invention is particularly suitable for in vitro detection of *Neisseria meningitidis* serogroup X by immunochromatography.

An important feature of the antibodies and fragments of the invention is that their binding to the capsular polysaccharides of *Neisseria meningitidis* serogroup X is specific, inter alia the antibodies and fragments of the invention do not bind to the capsular polysaccharides of the other serogroups of *Neisseria meningitidis*. The terms "specifically bind" mean that the antibodies and fragments of the invention bind to *Neisseria meningitidis* serogroup X, as expressed on the coated surface of *Neisseria meningitidis* serogroup X bacteria, and do not bind to polysaccharides of other *N. meningitidis* serogroups or of other bacteria, especially encapsulated bacteria.

The monoclonal antibodies according to the invention thus do not cross react with other types of bacteria; especially they do not cross react with *E. coli, H. influenza, S. pneumonia*. The monoclonal antibodies also do not cross react with any serogroup of the *N. meningitidis* other than serogroup X. Inter alia, they do not cross-react with any of the 11 other serogroups identified for *N. meningitidis*, namely serogroups A, B, C, Y, W (previously known as W135), Z, E (previously known as 29E), H, I, K and L; preferably they do not cross react with the other 5 most widespread serogroups of *N. meningitidis*, namely A, B, C, W and Y.

The monoclonal antibodies of the invention are thus highly specific for the serogroup X of *Neisseria meningitidis* and therefore allow the specific detection of this serogroup and allow distinction between this serogroup and any other serogroup. In this respect, it is to be mentioned that the specificity of the monoclonal antibodies of the invention is a feature which is imparted by the sequences of the 6 CDR set forth in SEQ ID No 1-6.

By way of contrast, most of the antibodies against NmX known before the present invention, are not entirely specific for NmX and thus have been disclosed as cross-reacting with other serogroups of *N. meningitidis* (Afssaps report, 25 Nov. 2009, by Dr Natacha Charler-Bret); or their specificity has not been tested against all the *N. meningitidis* serogroups. Moreover, none of the prior monoclonal antibodies against NmX has been validated for the detection of soluble antigens from NmX, especially without prior purification, contrary to the monoclonal antibodies of the invention.

A monoclonal antibody or a fragment thereof according to the invention preferably comprises a heavy chain region comprising an amino acid sequence set forth in SEQ ID No 7 or in SEQ ID No 8, or variants thereof, having at least 90% sequence identity and identical CDRs.

It is also preferred that a monoclonal antibody or a portion thereof according to the invention comprises a light chain region comprising an amino acid sequence set forth in SEQ ID No 9, or variants thereof, having at least 90% sequence identity and identical CDRs.

Preferred monoclonal antibodies or fragments thereof according to the invention are those comprising a heavy chain region comprising an amino acid sequence set forth in SEQ ID No 7 and a light chain region comprising an amino acid sequence set forth in SEQ ID No 9, and those comprising a heavy chain region comprising an amino acid sequence set forth in SEQ ID No 8 and a light chain region comprising an amino acid sequence set forth in SEQ ID No 9. A monoclonal antibody of the invention is for example the antibody secreted by the hybridoma cell line or cell culture K1-5 deposited at the CNCM (Collection nationale de cultures de micro-organismes (CNCM) Institut Pasteur; 25-28, rue du Docteur Roux; 75724 Paris Cedex 15 FRANCE), on 21 May 2015, under accession number I-4983.

This hybridoma has been obtained as described in the experimental section, by immunizing mice with whole inactived *N. meningitidis* serogroup X and fusion of immortalised myeloma cell (plasmacytoma P3U1) with splenocytes from the immunised mice. The antibody is either purified from the hybridoma culture medium or purified from ascitis, for example using water purification.

According to another embodiment, a monoclonal antibody of the invention is the antibody secreted by the hybridoma cell line or cell culture K7-1 deposited at the CNCM (Collection nationale de cultures de micro-organismes (CNCM) Institut Pasteur; 25-28, rue du Docteur Roux; 75724 Paris Cedex 15 FRANCE), on 21 May 2015, under accession number I-4984. This hybridoma has been obtained as described in the experimental section, in the same fusion as K1-5. The antibody is also either purified from the hybridoma culture medium or purified from ascitis, for example using water purification.

The antibodies K1-5 and K7-1 are immunoglobulins M.

The 6 CDRs characterizing the monoclonal antibodies of the invention, or antigen-binding portions thereof, are those of the antibodies produced by the deposited cell lines. These 6 CDRs may thus be defined either by reference to SEQ ID No 1-6 of the enclosed sequence listing, or by reference to the 6 CDRs of the two antibodies K1-5 and K7-1 deposited at the CNCM under accession number I-4983 and I-4984 respectively.

According to one aspect of the invention, the antigen-binding portion of a monoclonal antibody of the invention may be or may comprise a Fab fragment, corresponding to the entire light chain and corresponding part of the heavy chain. Fab fragment comprises the antigen-binding site.

According to another aspect, the antigen-binding portion of a monoclonal antibody of the invention may be or may comprise a Fab' fragment. In the context of the invention, a Fab' fragment is a Fab fragment in which the heavy chain additionally comprises the natural hinge region on its carboxy terminal, suitable for covalent bonding to a second antibody fragment. The hinge contains one or more amino acid residues or chemical groups which are suitable for covalent bond formation, for example a free cysteine, thereby allowing dimerisation of the Fab' fragment. Alternatively, the Fab' fragment may be artificially dimerized.

The advantage of using Fab' fragments is that they can be dimerised to form F(ab')$_2$ fragments having two antigen binding domains. F(ab')$_2$ fragments are therefore divalent, increasing avidity of binding with respect to a Fab monomer.

According to a further embodiment of the invention, the antibody fragment of the invention may be or may comprise a Fab, Fab' or a F(ab')$_2$ fragment, preferably a Fab portion of an IgM, most preferably of K1-5 or from K7-1.

Any fragment of monoclonal antibody according to the invention at least comprises the 6 CDRs set forth in SEQ ID No 1 to 6 or the 6 CDRs of the antibodies excreted by the deposited cell lines I-4983 and I-4984.

The antibodies and portions of the invention may be fully of murine origin or fully human. Alternatively, the antibodies and fragments thereof according to the invention may combine for example a heavy chain of non-human origin, for example murine, with a light chain of human origin, or the chains may be chimeric, or antibody engineering techniques may be used to humanise the heavy chain and/or the light chain, or both.

A monoclonal antibody or fragment thereof according to the invention is preferably a murine antibody or fragment thereof, but may also be a human, rabbit, humanized or chimeric antibody, or fragment thereof.

It is to be noted that a monoclonal antibody or antigen-binding portion according to the invention, is advantageously purified, or isolated from other distinct antibodies, especially it is not part of a polyclonal serum comprising different antibodies. Preferred also are purified monoclonal antibodies or antigen-binding portions according to the invention.

The invention also concerns cells producing, synthesizing or secreting an antibody of the invention, or portion thereof as defined above, especially isolated cells or clonal population. Preferably, such cells do not produce other antibodies, especially do not produce other antibodies directed to NmX. Preferred cells are the hybridomas, inter alia the hybridoma cell lines deposited at the CNCM disclosed above.

The invention is also directed to a diagnostic agent, corresponding to the monoclonal antibody of the invention, specific for NmX capsular polysaccharide, linked to a detection label. The linkage between the monoclonal antibody and the detection label can be any sort of linkage, either directly, or indirectly, for example via another molecule or support. The linkage may be a non-covalent linkage, for example based on electrostatic forces, or may be a covalent linkage.

A detection label as used here consists in or comprises preferably a reporter group, selected for example from enzymes, substrates, cofactors, inhibitors, dyes, radioisotopes, luminescent groups, fluorophores, colorimetric indicators, gold particles, latex particles, and biotin. Any other reporter group may also advantageously be used. Such a reporter group allows the revelation of the detection label and thus of the antibodies linked to said detection label. The way of revealing the reporter group is dependent of course on the reporter group.

When used for therapeutic applications, the antibody or fragment thereof according to the invention, is conjugated to an effector moiety such as a cytotoxic agent.

In the context of the present invention, the monoclonal antibody is preferably linked to gold particles, especially when it is to be used in rapid diagnostic test such as a dipstick test. In this way, it can be visualized on a solid support without difficulty, without the need for specific equipment, and very rapidly.

The monoclonal antibodies according to the invention are indeed specifically suitable for soluble detection of antigens of NmX, thus allowing the specific detection of NmX, i.e. allowing the discrimination of serogroup X from other serogroups.

According to a second aspect, the present invention is thus directed to different methods for the detection of NmX, or of NmX capsular polysaccharides, the detection being specific for serogroup X, allowing the discrimination between this serogroup and other serogroups of *Neisseria meningitid Indeed, the monoclonal antibodies of the invention, or antigen-binding portions thereof, are advantageously used as immunological probes to specifically detect the NmX bacteria. According to one embodiment of said method, the detection is to be made in a sample, preferably a clinical sample of a biological fluid, inter alia obtained from a patient affected or suspected to be affected by meningitis infection; i.e. without a culture step. Such a method comprises the step of contacting the fluid with monoclonal antibodies or portions thereof according to the invention or with the diagnostic agent of the invention, and the step of determining the presence or absence of NmX antigens in the fluid.

The method as described is preferably to be carried out in vitro or ex vivo. The first step of contacting the fluid with the monoclonal antibody or antigen-binding portion thereof is thus made in vitro or ex vivo. The monoclonal antibodies, or their fragments as defined according to the invention, are advantageously linked to a detection label, as disclosed above.

The antigens of NmX are polysaccharides of NmX, specifically capsular polysaccharides of NmX. The antigens likely to react with the monoclonal antibodies or fragments of the invention are advantageously soluble antigens of NmX present in the biological fluid, inter alia blebs.

The monoclonal antibodies are preferably IgG or IgM, more preferably K1-5 or K7-1, or antigen-binding portions thereof as described, especially portions comprising Fab, Fab' or $F(ab')_2$ fragment of K1-5 or K7-1.

The presence or absence of NmX antigens can be determined by any appropriate means known to the skilled person in the art; this depends mainly on the detection label attached to the monoclonal antibody or fragment thereof according to the invention. According to a preferred embodiment, the presence or absence of soluble antigens of NmX can be determined by simple visual inspection, for example of the fluid sample in the presence of the monoclonal antibodies, or by visual inspection of a solid support previously contacted with the biological sample and with the monoclonal antibodies. Alternatively, any other appropriate means can be used, for example in order to quantify the interaction between the monoclonal antibodies, or antigen-binding portions thereof as defined in the present invention, and the biological fluid sample.

According to a preferred embodiment of the method, the second step of determining the presence or absence of NmX is carried out by detection of the presence or absence of a complex, specifically an immune complex, formed between the monoclonal antibodies, or antigen-binding portion thereof and the soluble antigens of NmX.

In an embodiment, the method comprises the use of a detection component which is specific for the monoclonal antibodies or fragments thereof according to the invention, and thus allows the detection of said antibodies, even bound to their targets. As an illustration, if mouse monoclonal antibodies are used in carrying out the invention, the detection component is for example goat anti-mouse antibodies, thus allowing the detection of the presence of the monoclonal antibodies of the invention. According to this embodiment, the antigens of NmX present in the sample are preferably immobilized, such that the detection of the monoclonal antibodies or fragments of the invention, after washing steps, is indicative of the presence of NmX antigens.

In another alternative embodiment, the method comprises the use of a detection component which is specific for the NmX antigens, for example such a component may comprise a monoclonal antibody according to the invention, or an antigen-binding portion thereof as defined, or may comprise polyclonal antibodies specific for NmX, as described in the experimental section. As an illustration, if monoclonal antibodies linked to a detection label are used in the first step of contacting, polyclonal anti-cpsX antibodies, unlabelled but immobilized on a solid support, can for example be used to detect the presence of the complex between the labeled monoclonal antibodies of the invention and the soluble antigens of NmX.

Conversely, polyclonal antibodies linked to a detection label can be used in the first step of contacting the fluid, and monoclonal antibodies or fragments thereof according to the invention are used to detect the formation of the complex between the labeled polyclonal antibodies and the soluble antigens of NmX.

The method of the invention is to be used for the specific detection of NmX, i.e. the method allows the determination of whether antigens of NmX are present or absent from the sample under consideration, preferably biological fluid, independently of any other serogroups of *Neisseria meningitidis* or any other bacteria likely to be also present in said fluid.

The biological fluid to be used in carrying out the method is any appropriate biological fluid in which antigens of NmX are likely to be found in case of *meningitidis* infection. Appropriate fluids are for example cerebrospinal fluid, blood, urine, joint fluid, pericardial fluid and pleural fluid. The detection means are to be adapted to the fluid considered and to the concentration of NmX antigens likely to be present. Preferred biological fluids are cerebrospinal fluid, blood and urine, and most preferably cerebrospinal fluid.

The method can be carried out with IgM antibodies according to the invention, especially murine IgM antibodies, more preferably with one of the monoclonal IgM antibodies K1-5 and K7-1, secreted by I-4983 and I-4984 respectively.

According to a preferred embodiment, the invention is directed to an in vitro method for diagnosing a *Neisseria meningitidis* serogroup X infection in a subject, comprising carrying out the method as defined above, on a biological fluid sample from said subject. Preferably said subject is affected by *meningitidis* or is suspected to be affected, either because the subject presents some symptoms indicative of *meningitidis*, or because the subject has been in contact with affected persons.

According to this method of diagnosing, the presence of antigens of *Neisseria meningitidis* serogroup X in the sample is indicative of *Neisseria meningitidis* serogroup X infection.

The sample is preferably a sample of a biological fluid as detailed above, and especially a sample of cerebrospinal fluid, a sample of blood or a sample of urine. The volume of the sample may be very small, insofar as the method for diagnosing according to the invention does not require any step of culturing bacteria from said sample, a few mL can be sufficient or even a smaller quantity. For example, the sample is 150 μL of biological fluid when the method of diagnosing is carried out as described in Examples.

The sample used for carrying out the method of the invention has preferably been obtained from the subject under sterile conditions. It is highly preferred that the method is carried out in the hours following the sampling of the fluid. Alternatively, the sample can be stored under sterile conditions, preferably in the cold, until the diagnostic method of the invention is carried out.

The detection method as described may also be used for quantifying the presence of NmX polysaccharide in a sample. According to this embodiment, the method is carried out for example on a sample intended for immunization or vaccination, such that the monoclonal antibodies of the invention are used to quantify the NmX antigen present in the sample.

According to a third aspect, the present invention is directed to a diagnostic kit for detecting *Neisseria meningitidis* serogroup X. Such a diagnostic kit comprises monoclonal antibodies or antigen-binding portions thereof according to the invention, or said monoclonal antibodies or fragments linked directly or indirectly, covalently or non-covalently to a detection label, corresponding to a diagnostic agent as defined above. The monoclonal antibodies according to the invention, or their antigen-binding portions, are either in a free, soluble form, or are immobilized on a support. The antibodies may advantageously be monoclonal IgM antibodies, inter alia K1-5 and K7-1, secreted by I-4983 and I-4984 respectively.

According to a preferred embodiment, the kit also comprises a means for detecting the production of an immune complex between said antibodies and antigens of NmX. Such means can be of any type, it can be for example antibodies specific for one or the other partner of the immune complex, i.e. either antibodies directed to the capsular polysaccharides of NmX, or antibodies directed to the monoclonal antibodies of the kit. Suitable means also comprise any means detecting the formation of a complex on the basis of the properties of the immune complex formed, for example its weight, its size, etc.

Alternatively, a diagnostic kit for detecting *Neisseria meningitidis* serogroup X comprises:
  a first antibody, specifically recognizing NmX, linked directly or indirectly, covalently or non-covalently to a detection label, either in a free, soluble form, or immobilized on a support and
  a detection antibody for detecting the production of an immune complex between said first antibody and antigens of NmX,
wherein either the first antibody, or the detection antibody, or both, are a monoclonal antibody, or a fragment thereof, according to the invention.

According to one embodiment, the diagnostic kit according to the invention may comprise:
  polyclonal antibodies specifically recognizing NmX, linked directly or indirectly, covalently or non-covalently to a detection label, either in a free, soluble form, or immobilized on a support and
  monoclonal antibodies or fragments thereof according to the invention.

Conversely, according to a preferred embodiment, the diagnostic kit comprises monoclonal antibodies or fragments thereof as defined, both as first and as detection antibodies.

According to a preferred embodiment of the diagnostic kit of the invention, the kit is for detecting NmX in a biological fluid sample, without any culture step, especially without bacteria culture. Such a kit can for example be used immediately after sampling, without the usual delay due to the culture in case of serogroup X detection.

Adequate biological fluid samples have been detailed above, it includes cerebrospinal fluid, blood, urine, joint fluid, pericardial fluid and pleural fluid. Preferred fluids for the diagnostic kits of the invention are cerebrospinal fluid, blood and urine, and more preferably cerebrospinal fluid.

According to preferred embodiments, the detection is carried out by immunoassay, taking advantage of an immunological reaction of NmX antigens with the monoclonal antibodies of the invention, inter alia with IgM antibodies of the invention.

In this respect, any immunoassay can be used in the context of the present invention, to detect antigens of NmX in a biological fluid sample, either in a qualitative (positive or negative) or quantitative (amount measurement) manner. Many different immunoassays have been developed, which are highly adaptable and can be applied to many different formats, depending on the needs of the end user; these different tests are all applicable in the context of the present invention, taking advantage of the high specificity and sensitivity of the monoclonal antibodies or fragments thereof according to the invention.

In addition to the antibodies to be used, namely the monoclonal antibodies or binding fragments thereof according to the invention, the second feature of an immunoassay is the technology and the system which are to be used to detect the binding of the antibodies to the target analyte, namely soluble antigens of NmX.

Originally, the signal from an immunoassay resulted from an enzyme, to be bound to the complex formed by the antibodies and the target antigens, acting on a substrate to yield a colored solution, wherein the intensity of the coloration is indicative of the amount of target antigen in the test solution.

More recently new immunoassays have been developed, compressing the many steps of the previously designed immunoassays into a simplified format for the end user. One of such simplified formats is the nitrocellulose test strip. In this format, binding of the antibody to the target antigen can be directly observed, by the naked eye, due to the accumulation of dyed microbeads that will bind to a specific location on the nitrocellulose yielding a colored line, in case of presence of the target antigens in the solution to be tested.

Other immunoassays have been developed with improved sensitivity, allowing the detection of single molecules in a body sample. To this end, microscopic beads coated with the antibodies are added to the body sample to be analyzed, in order to capture the target antigens; the thus formed immunocomplexes are then labeled with an enzymatic reporter capable of generating a fluorescent product (27).

Other classical immunoassays which are well known and can be used in the context of the present invention are radioimmunoassay and Fluorescent Immunoassays. The key variable is the biochemical technique used for detecting the binding of the "detection" antibody, inter alia the monoclonal antibodies of the invention, and the soluble antigens of NmX.

Immunoassays are thus designed in many formats and the skilled person will know how to determine the most suitable immunoassays depending on the sample types including serum, plasma, whole blood, urine, or cerebrospinal fluids.

Preferred immunoassays are those which can be carried out rapidly and those which are extremely sensitive.

Immunoassays which can be advantageously used in diagnostic kits according to the invention are those relying on agglutination. In agglutination tests, a particle (latex bead or bacterium) is coupled to the monoclonal antibodies or fragments thereof according to the invention. The resulting particle complex is mixed with the sample of biological fluid to be analyzed; if the target antigen, namely soluble antigens of NmX is present in the sample, it cross-links the particles, producing measurable agglutination.

Usually, agglutination tests are rapid but less sensitive than many other methods.

A particularly preferred agglutination test is latex agglutination test. This test uses latex particles, coated or coupled with the monoclonal antibodies of the invention, or fragments thereof as defined. Presence of the polysaccharides of NmX leads to the agglutination of the coated latex particles. A kit of the invention according to this embodiment thus comprises the monoclonal antibodies of the invention, or fragments thereof as defined, coated on latex particles.

According to another embodiment, the diagnostic kits of the invention are based on an enzyme-linked immunosorbent (ELISA) test. In ELISA test, the sample is immobilized on a solid support, usually a polystyrene microtiter plate and the monoclonal antibodies or fragments thereof according to the invention are used as detection antibody, forming a complex with the antigens of NmX, if present.

In such a case, the monoclonal antibodies present in the kits are preferably linked to an enzyme, or the kits comprise antibodies specific to the monoclonal antibodies of the invention and linked to an enzyme.

According to a specific embodiment, the kit is suitable for use in the Simoa™ (single-molecule array) technology (27). For such a purpose, the monoclonal antibodies according to the invention, used as capture antibodies, are attached to the surface of paramagnetic beads. According to this technology, these beads are then contacted with the sample, potentially comprising soluble NmX antigens. The beads are then washed to remove proteins non-specifically bound and incubated with a detection antibody linked to an enzyme. Such a detection antibody is either polyclonal antibodies or monoclonal antibodies or fragments thereof according to the invention.

The kits according to this embodiment comprise the monoclonal antibodies of the invention, or antigen-binding portions thereof, linked to beads, preferably paramagnetic beads, as capture antibodies, and also the monoclonal antibodies of the invention, or polyclonal antibodies, linked to an enzyme, as detection antibodies.

Alternatively, the kits may comprise polyclonal antibodies, as described in the experimental section, linked to beads, preferably paramagnetic beads, and monoclonal antibodies according to the invention, linked to an enzyme, as detection antibodies.

According to still another embodiment, the kits of the invention are suitable for rapid diagnostic tests, especially lateral or vertical flow assays, also known as immunochromatographic assays; more preferably they are conceived as dipstick tests. According to this embodiment, the kit thus comprises antibodies, linked to gold particles, as detection antibodies, and also antibodies not-linked to gold particles immobilized in a specific area of a support, as capture antibodies, wherein either the capture antibodies, or the detection antibodies are monoclonal antibodies or antigen-binding portions thereof, according to the invention. Preferably both the capture and the detection antibodies are monoclonal antibodies or portions thereof according to the invention. Polyclonal antibodies, specifically binding NmX capsular polysaccharides, for example as described in the experimental section, can advantageously be used as detection or as capture antibodies, but preferably as detection antibodies.

The diagnostic kits of the invention are preferably stable at temperature up to 30° C., preferably up to at least 40° C., or up to at least 45° C.

Many other technologies can be used for the diagnostic tests of the invention and the technologies detailed above are for illustrative purpose only.

Depending on the technology to be used for demonstrating the presence of soluble antigens of NmX in the sample with the monoclonal antibodies of the invention, several additional components can be present in the diagnostic kits as described.

According to a preferred embodiment, the kit of the invention further comprises a solid support, on which the monoclonal antibodies of the invention, or polyclonal antibodies, either linked to a detection label or not, may be immobilized, but not necessarily. The diagnostic kit according to the invention may comprise inter alia a microtiter plate, a diagnostic platform, a nitrocellulose membrane or a miniaturized lateral or vertical flow device. A diagnostic platform may comprise a membrane, for example a charged membrane, plastic, beads, strips, microtiter wells, microchannels or a combination thereof.

The kits of the invention may comprise an immunochromatographic test strip, miniaturized lateral or vertical flow device, or enzyme-linked immunosorbent assay platform.

Depending on the technology to be used for revealing the potential presence of soluble antigens of NmX, the kits of the invention may also comprise a fluid receiving zone or chamber, preferably in or on the diagnostic platform.

The skilled person will adapt without difficulty the components of the kits, depending on the chosen technology for detecting the presence of soluble polysaccharides of NmX in the biological fluid sample to be tested.

According to a preferred embodiment of the invention, the diagnostic kit allows the detection by enzyme-linked immunosorbent assay at subfemtomolar concentration, for example at a concentration of 1 fM or below, for example of at a concentration of 0.5 fM of polysaccharide of NmX in the sample, or even below. In order to obtain such a low detection concentration, the technology to be chosen for the detection of soluble antigens of NmX is preferably the Simoa™ technology as detailed above. The advantages of this high sensitivity are that a very early detection can be carried out, for example before apparition of any symptom. This is especially useful for detecting infection in persons who have been in contact with affected patients.

According to a particularly preferred embodiment of the kits, the present invention is directed to a dipstick diagnostic test for NmX. Such a test comprises a membrane, preferably a nitrocellulose membrane. This membrane advantageously comprises the following zones:

a. a first zone comprising detection antibodies specifically binding NmX, linked directly or indirectly, covalently or non covalently to a detection label;
b. a capture zone comprising immobilized antibodies specifically binding NmX, as capture antibodies, and.
c. optionally a control zone comprising an immobilized control polypeptide.

In the dipstick diagnostic test as described, either the detection antibodies, or the capture antibodies, or both the detection and the capture antibodies are monoclonal antibodies according to the invention, or fragments thereof as defined. Preferably, both the detection antibodies and the capture antibodies are monoclonal antibodies or antigen-binding portions according to the invention.

The biological fluid sample to be tested is brought into contact with one extremity of the membrane. The sample then migrates along the membrane, either vertically or laterally depending on the system, first through the $1^{st}$ zone where soluble antigens of NmX, if present in the sample, will bind to the detection antibodies. As the sample flows through the Capture zone, the immune complex, formed by the detection antibodies and the antigens of NmX, will bind to the immobilized capture antibodies, provided that soluble antigens of NmX are present in the sample, thus capturing and immobilizing the detection label linked to the detection antibodies in a specific area of the membrane. Otherwise, no detection label is captured by the capture antibodies. As the sample flows through the control zone, the detection antibodies linked to the detection label will bind to the control zone, irrespective of whether they are bound to soluble antigens of NmX.

It is thus imperative that the sample flows through the first zone before flowing through the capture or control zone; the respective disposition of the capture and control zones is not critical.

According to a preferred embodiment, the first zone as defined above comprises the diagnostic agent as defined in the context of the present invention. It is particularly preferred that the detection antibodies are conjugated, preferably by covalent binding, to gold particles, for the detection. According to one embodiment, the detection antibodies are polyclonal antibodies, as described in the experimental section. According to another embodiment, the detection antibodies are monoclonal antibodies or antigen-binding portions thereof, as defined in the invention, especially IgM antibodies or portions of the invention.

With respect to the control zone, the immobilized control polypeptides are advantageously control antibodies, especially antibodies capable of recognizing the antibodies of the first zone irrespective of whether said antibodies are conjugated to gold particles, and irrespective of whether these antibodies are linked to their specific antigen, namely linked to polysaccharides of NmX. According to a preferred embodiment, when the detection antibodies have been obtained by immunization of a specific mammal, for example by immunization of a mouse, the control polypeptides are antibodies specifically directed to antibodies of said mammal, for example they are goat anti-mouse antibodies. Of course, depending on the detection antibodies used in the first zone of the membrane, the control polypeptides are to be adapted in order to recognize these antibodies.

Regarding the capture zone of the membrane, it comprises capture antibodies, which are not linked to the detection label of the antibodies present in the first zone. Preferably they are not linked to any detection molecule of any type. Particularly preferred capture antibodies are monoclonal antibodies of the invention, or antigen-binding portions thereof according to the invention, especially IgM antibodies or portions of the invention.

Suitable means for immobilizing the control polypeptides of the control zone and the antibodies of the capture zone are well known to the skilled man. By definition, the antibodies of the first zone are not immobilized on the membrane and constitute a mobile phase.

The different zones of the dipstick test are preferably distinct and not overlapping before use of the dipstick.

According to one embodiment, the detection antibodies are polyclonal antibodies specifically binding NmX capsular polysaccharides and the capture antibodies are monoclonal antibodies of the invention, or antigen-binding portions thereof according to the invention.

According to another embodiment, the detection antibodies are monoclonal antibodies of the invention, or antigen-binding portions thereof according to the invention, and the capture antibodies are polyclonal antibodies specifically binding NmX capsular polysaccharides. According to a preferred embodiment, the detection and capture antibodies are monoclonal antibodies of the invention, or antigen-binding portions thereof according to the invention; they are either identical or distinct. Preferred antibodies are IgM antibodies, such as K1-5 and K7-1 antibodies. The inventors have indeed designed for the first time a dipstick test using only IgM antibodies, both as detection and as capture antibodies.

For example, the detection antibodies are K1-5 and the capture antibodies are K7-1, or the opposite.

The dipstick test of the invention is simple, convenient, quick and concise and does not require special equipment and facilities as well as professional training. Furthermore, the dipstick has clear and easy-identity results, simple operation and easy popularization, is applicable to matrixes, field tests of emergency on a large scale and the study of epidemiology and can aid in the infection diagnostics.

The diagnostic test or dipstick test according to the invention is preferably characterized by a sensitivity (Se) of at least 85%, preferably at least 90%. According to another preferred embodiment, the diagnostic kit or test according to the invention has a specificity (Sp) which is at least 85%, preferably at least 90%.

According to another preferred embodiment of the invention, the diagnostic kit or test has a detection limit of the NmX capsular polysaccharide below 50 ng/mL, preferably below 10 ng/mL, preferably below 5 ng/mL, especially around 2.5 ng/mL or less, or less than 1 ng/mL, especially in case of use of the Simoa™ technology.

According to another preferred embodiment of the invention, the diagnostic kit or test has a detection limit of NmX bacteria of around $10^5$ CFU/mL or below, preferably of $10^4$ CFU/mL or below, most preferably around $5\times10^3$ CFU/mL or below, inter alia $3.5\times10^3$ CFU/mL.

According to another aspect, the present invention also concerns the use of a diagnostic kit or test as defined above, preferably for the in vitro diagnostic of NmX infection in the biological sample of a subject. Said subject may be suspected of meningitis infection, or may have been in contact with infected patients.

The biological sample which can be used in this context is as defined in the other aspects of the invention, inter alia it is preferably a sample of cerebrospinal fluid, urine or blood.

The other preferred embodiments are as detailed above, regarding to other aspects of the invention.

The invention is also directed to the use of a monoclonal antibody according to the invention, or an antigen-binding fragment or portion thereof as defined above, specifically binding NmX, for detecting in vitro *Neisseria meningitidis* serogroup X capsular polysaccharides or *Neisseria meningitidis* serogroup X bacterium, preferably in a liquid sample, most preferably a biological liquid sample. It is particularly preferred that the detection is carried out by immunochromatography.

The invention also concerns the use of the monoclonal antibodies or portions thereof as defined, as a standard for characterizing and quantifying NmX in sample. It is indeed noted that none reproducible monoclonal antibody, sufficiently sensitive and specific for NmX, is presently available as standard.

In all the embodiments described herein, antigen-binding portions of the monoclonal antibodies of the invention can advantageously replace monoclonal antibodies of the invention; such antigen-binding portions being preferably Fab, Fab' and $F(ab')_2$ as described above.

LEGENDS OF FIGURES

FIG. 1. Dot blotting analysis of rabbit sera. Sera from two rabbits prior to immunization (day 0) and 7 days after injection of the third dose of NmX strain 19504 (day 28) were used at 1:1000 dilutions in immunoblotting. Four meningococcal isolates were spotted at $2.10^5$ colony forming units, CFU/mL (1: strain 19404, 2: strain 23557, 3: strain 24196, 4: strain 24287).

Figure 2:
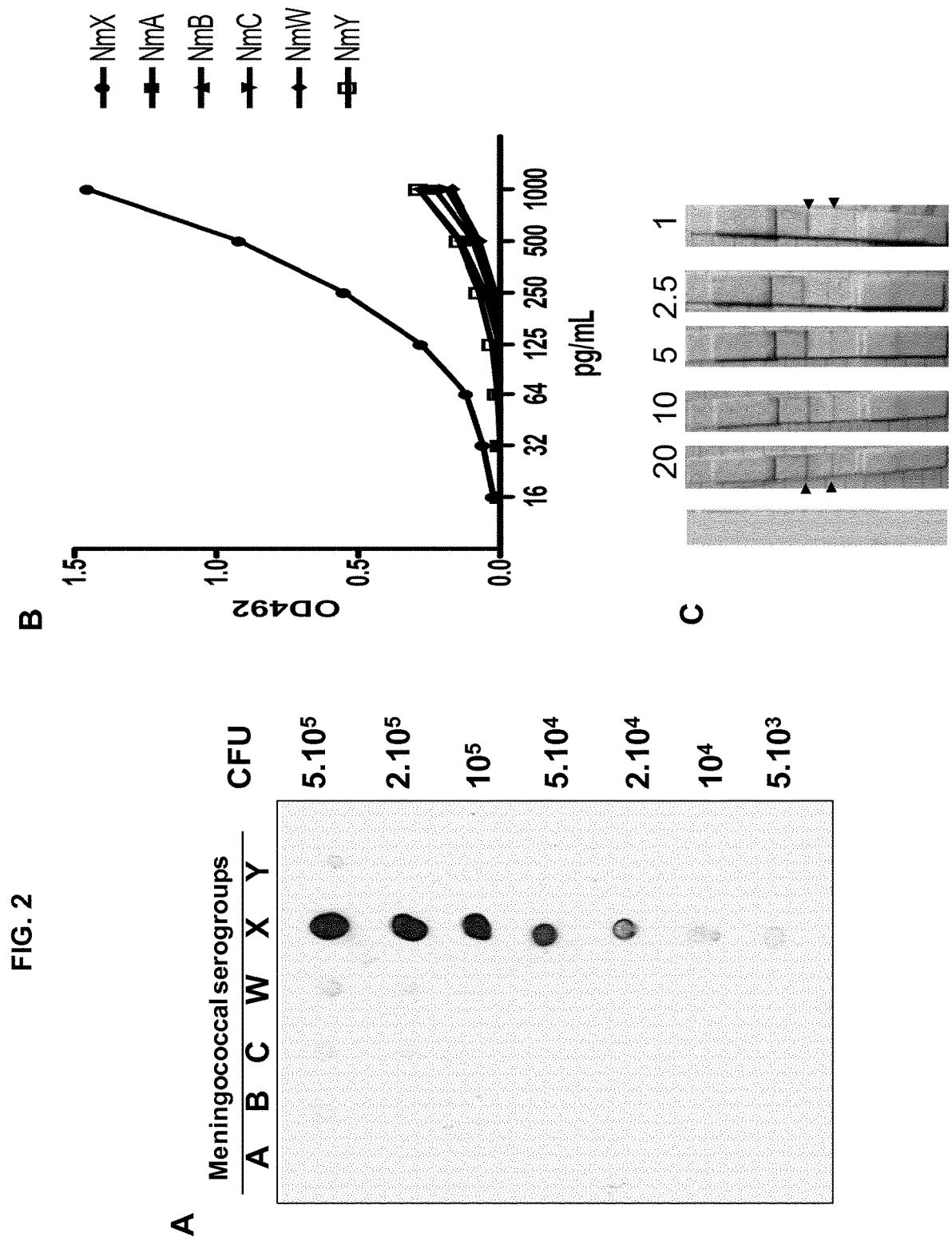

FIG. 2. Specific recognition of the purified rabbit anti-cpsX IgG antibodies. (A) Dot blotting analysis against whole bacteria. Serogroups are indicated above the dots and amounts of loaded bacteria in each spot are indicated on the right (in colony forming units, CFU). Antibodies were used at a final concentration of 500 µg/mL. (B) ELISA analysis using coated purified capsular polysaccharide for serogroups A, B, C, Y, W and X (Table 1). Data are expressed as OD 492 nm absorption for each concentration of antibodies (in pg/mL). Data correspond to the means of two independent experiments. The corresponding serogroups are indicated on the right. (C) Detection cut-off value for purified cpsX. The amounts are indicated in ng above each dipstick. A dipstick, before use, is shown on the left. The upper two arrows indicate the capture control line corresponding to the goat anti-rabbit IgG. The lower two arrows indicate the capture line corresponding to the anti-cpsX-specific IgG (cpsX line).

Figure 3:
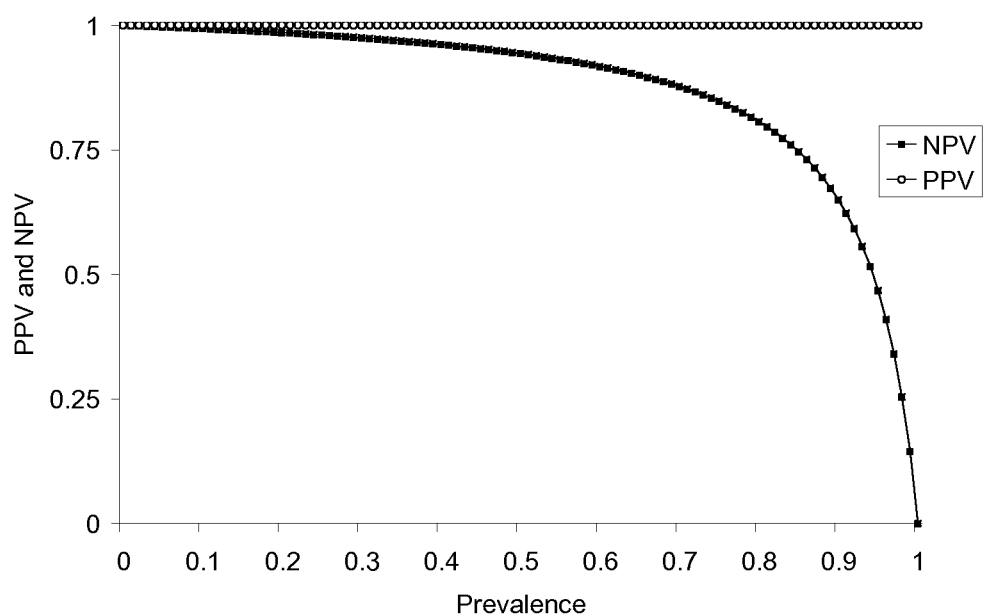

FIG. 3. Predictive values for N. meningitidis diagnosis. Positive Predictive Values and Negative Predictive Values (PPV and NPV, respectively) for the diagnosis of NmX were calculated according to a disease prevalence ranging between 0 and 100%.

Figure 4A:
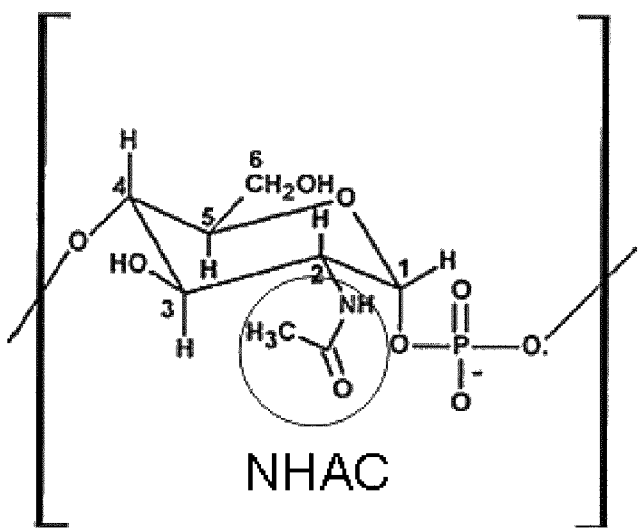
Figure 4B:
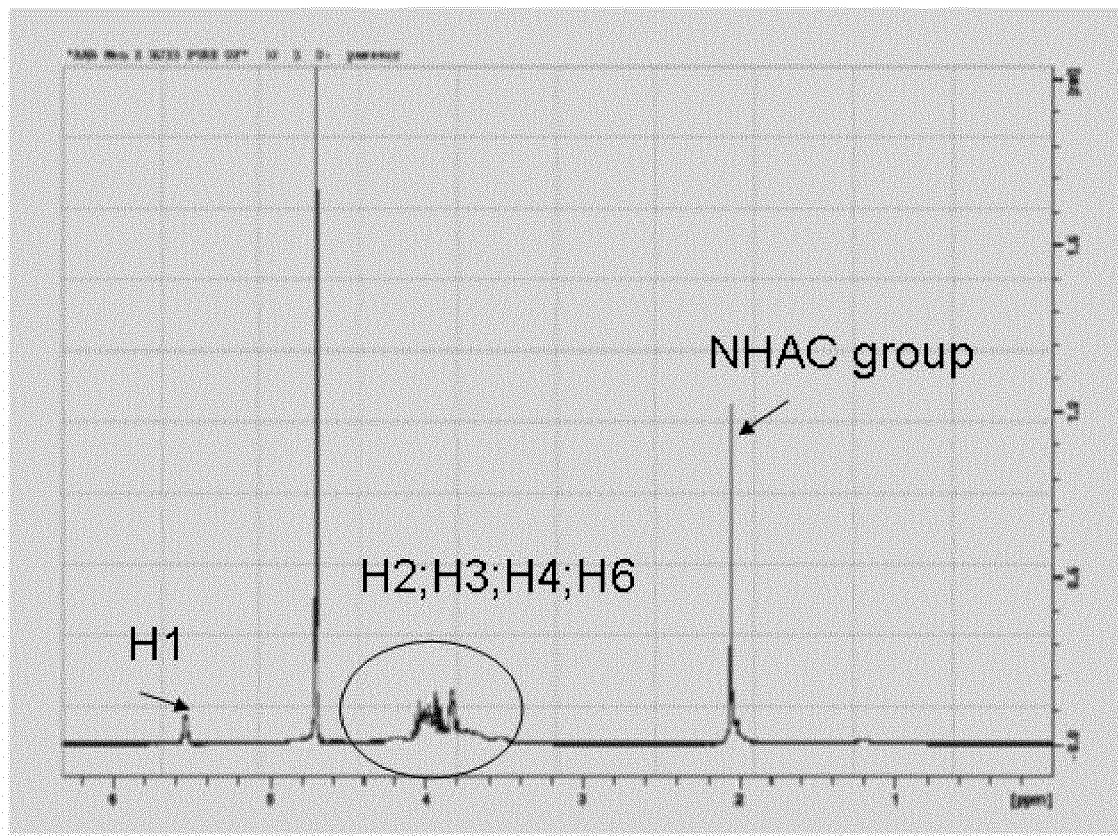

FIG. 4. FIG. 4A: structure of the capsular polysaccharide of meningococci serogroup X: homopolymer of 1→4-linked N-acetyl-D-glucosamine 1-phosphate. FIG. 4B: 1H NMR spectrum recorded on a Bruck Avance 400 spectrometer type, with a frequency of 400 MHz. The sample was dissolved in deuterium oxide ($D_2O$). The chemical shifts (δ) are expressed in parts per million (ppm) and the reference used is the 4,4-dimethyl-4-silapentane 1-sulfonic acid (DSS). The coupling constants are given in Herz (Hz). The peaks are indicated according to the position (1 to 6) on the repeated units of the cpsX (see FIG. 4A).

Figure 5:
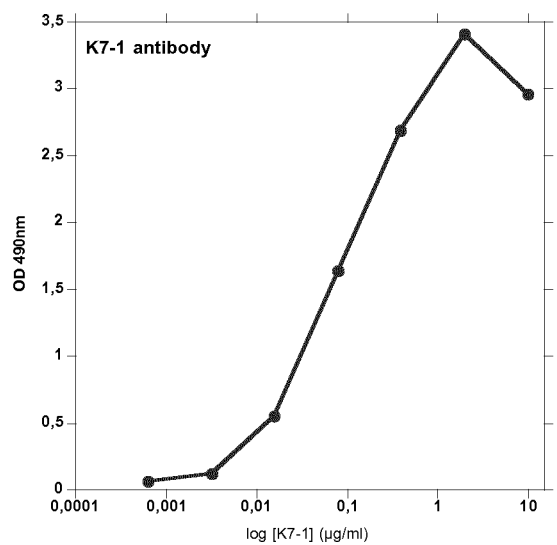

FIG. 5. ELISA dose-response curves of K7-1 antibodies on cpsX coated plates. Along the x-axis is reported the antibody concentration in pg/ml. Along the y-axis is reported the optical density (OD), at 490 nm. Identical results were obtained for the K1-5 antibodies.

Figure 6:
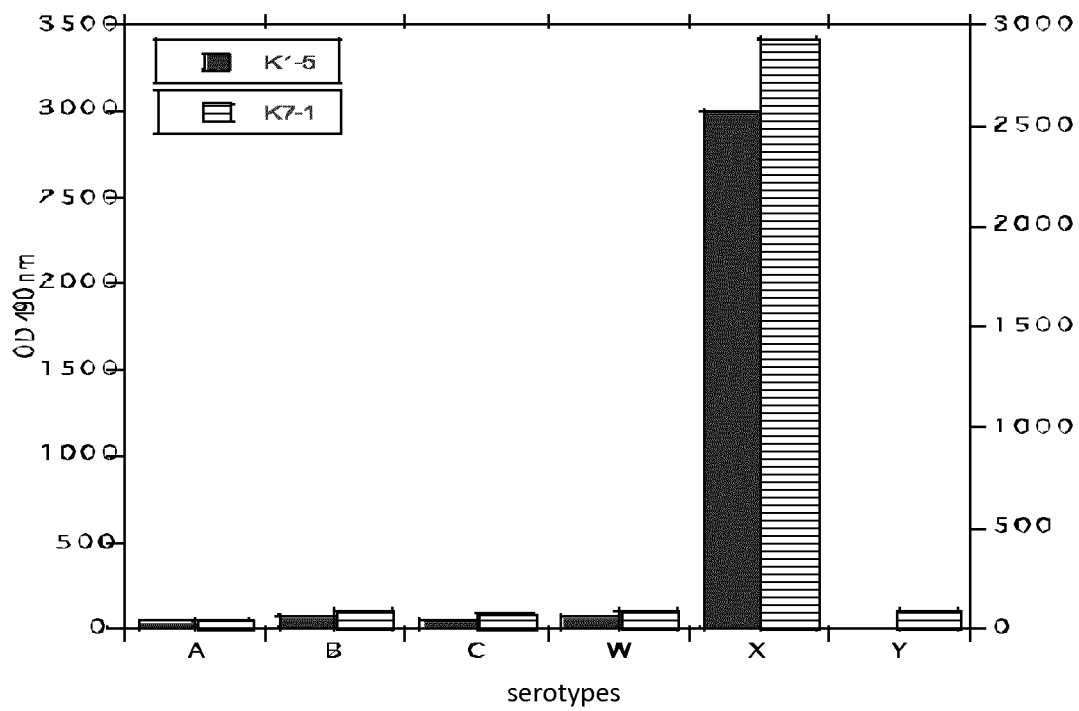

FIG. 6. ELISA recognition by the K1-5 (black) and K7-1 (hatched) antibodies (1 µg/ml) of coated capsules originating from different Neisseria meningitidis serogroups. X-axis: N.m. serogroup. Y-axis: Optical Density at 490 nm.

FIG. 7. Dot blot recognition of different serogroups of bacteria by the K1-5 antibody (5 µg/ml). Twofold serial dilutions of bacteria (expressed in CFU on the right of the blot) were spotted vertically. The serogroup of bacteria are indicated on the top of the blot column.

FIG. 8. Amino-acid sequence of the CDR regions of K1-5 (K1) and K7-1 (K7) coding genes. The CDRs (CDR1, 2 and 3 from 5' to 3') of the heavy (H) and light (L) chains are underlined. SEQ ID No 1, 2 and 3 correspond to CDR1, CDR2 and CDR3 respectively of the heavy chain, and SEQ ID No 4, 5 and 6 correspond to CDR1, CDR2 and CDR3 respectively of the light chain.
SEQ ID No 7 corresponds to amino acids 1-120 of the heavy chain of K1-5; SEQ ID No 8 corresponds to amino acids 1-120 of the light chain of K7-1. SEQ ID No 9 corresponds to amino acids 1-120 of the light chain of K1-5 or K7-1.

Figure 9:
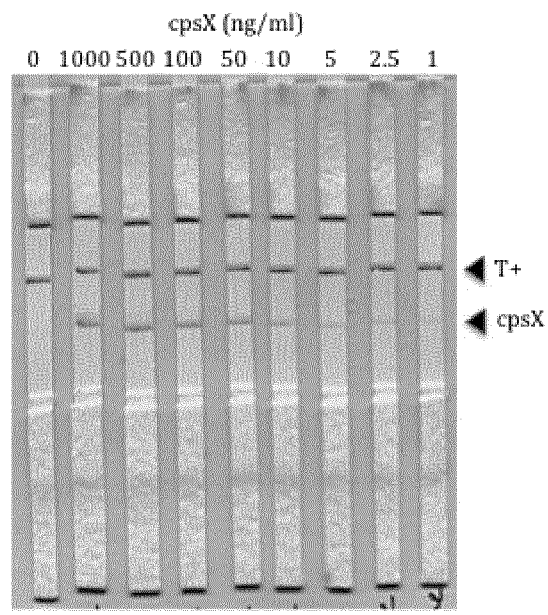

FIG. 9. RDT detection of Neisseria meningitidis X capsule (cpsX) using K7-1 as capture antibody and the rabbit polyclonal anti NmX antibody as gold conjugate. The cpsX concentration (ng/ml) of the tested sample is indicated on the top of the blot. T+ indicates the location of the migration control line (anti-rabbit IgG antibodies), and CA the location of the Capture Antibody line.

Figure 10:
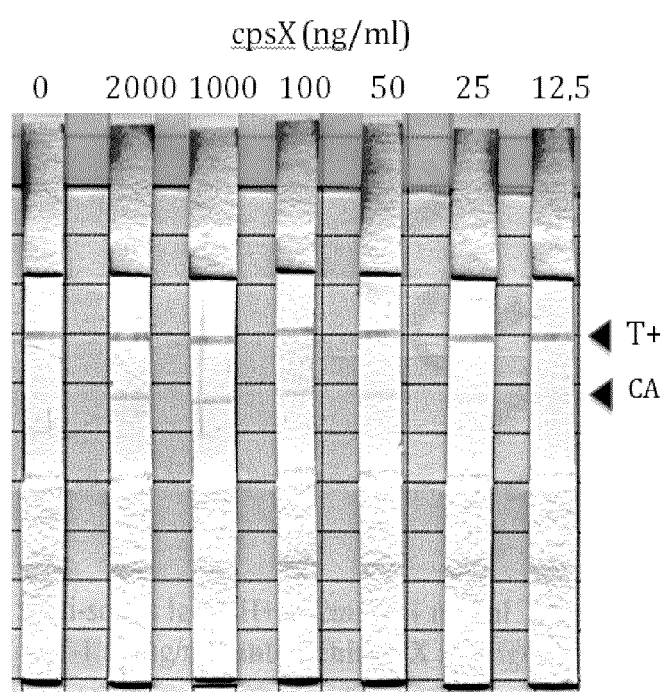

FIG. 10. RDT detection of Neisseria meningitidis X capsule (cpsX) using K1-5 as capture antibody and K7-1 as gold conjugate. The cpsX concentration (ng/ml) of the tested sample is indicated on the top of the blot. T+ indicates the location of the migration control line (anti-mouse IgG (H+L) antibodies), and CA the location of the Capture Antibody line.

EXAMPLES

The inventors have developed and evaluated a new rapid diagnostic test (RDT) for detecting the capsular polysaccharide (cps) antigen of this emerging serogroup, based on new monoclonal antibodies, or on monoclonal and polyclonal antibodies.

For the polyclonal antibodies, whole inactivated NmX bacteria were used to immunize rabbits. Following purification by affinity chromatography, the cpsX-specific IgG antibodies, were utilized to develop a NmX-specific immunochromatography dipstick RDT. The test was validated against purified cpsX and meningococcal strains of different serogroups. Its performance was evaluated against PCR on a collection of 369 cerebrospinal fluid (CSF) samples obtained from patients living in countries within the meningitis belt (Cameroon, Côte d'Ivoire and Niger) or in France. The RDT was highly specific for NmX strains. A cut-off of $10^5$ CFU/mL and 1 ng/mL was observed for the reference NmX strain and purified cpsX, respectively. Sensitivity and specificity were 94% and 100%, respectively. A high agreement between PCR and RDT (Kappa coefficient of 0.98) was observed. The RDT test gave a high positive likelihood ratio and a low negative likelihood (0.07) indicating almost 100% probability to declare disease or not when the test is positive or negative, respectively. This unique NmX-specific test could be added to the available set RDT tests for the detection of meningococcal meningitis in Africa as a major tool to reinforce epidemiological surveillance after the introduction of the NmA conjugate vaccine.

In order to improve this RDT, the inventors have then developed monoclonal antibodies, which can be used as a substitute for the polyclonal antibodies, or which can be used in association with the polyclonal antibodies, especially in the RDT developed by the inventors.

Example 1: Materials and Methods

Bacterial Strains and Samples

N. meningitidis isolates used in this study were isolates from cases of meningococcal disease (see Table 1 for details). Bacteria were cultured on GCB medium (GC Agar Base, Difco, Detroit Mich., USA) supplemented with Kellogg supplements (15). The serogroup was determined by agglutination with serogroup-specific antisera according to the standard procedure (16). Further phenotyping (serotyping and serosubtyping) was performed using monoclonal antibodies against the meningococcal proteins PorA and PorB as previously described (17). The cerebrospinal fluid (CSF) samples tested in this study corresponded to suspected bacterial meningitis cases. They were obtained from the National Reference Laboratories for Meningococci located at the Institut Pasteur of Côte d'Ivoire and at the Institut Pasteur, Paris, France, as well as from the Centre de Recherche Modicale et Sanitaire (CERMES) in Niamey, Niger, and from the Centre Pasteur of Garoua, Cameroon.

These samples were received in the frame of these centres' mission for the surveillance of meningococcal diseases in the corresponding countries under approvals from the internal board of the Institut Pasteur to collect, characterize and use these samples that are all anonymized.

The PCR analysis of these samples was used as a reference method to detect *N. meningitidis*, *Streptococcus pneumoniae* and *Haemophilus influenzae*, as well as to genogroup meningococcus-positive specimens. PCR conditions and primers were as previously described (8). Culture was not used as it has been constantly shown to be less sensitive than PCR (26). Culture data were available only for 26 of the 369 tested CSF samples.

TABLE 1

Strains used in the study and their characteristics

| Strain reference | Serogroup:serotype/serosub-type |
|---|---|
| 21525* | A:4:P1.9 |
| 21526 | A:4:P1.9 |
| 19256 | B:NT:P1.5, 2 |
| 19257 | B:2a:P1.5, 2 |
| 19324 | B:2b:P1.5, 2 |
| 21721* | B:NT:P1.4 |
| 22733 | B:15:P1.4 |
| 22590 | B:14:P1.7, 16 |
| 22644 | C:15:P1.7, 16 |
| 22639 | C:2a:P.5 |
| 20137 | C:2b:P1.5, 2 |
| 19008 | C:2a:P1.5, 2 |
| 20134 | C:NT:P1.10 |
| 19456 | Y:14:NST |
| 19336* | Y:NT:P1.5 |
| 19995* | W:2a:P1.5, 2 |
| 19481 | W:NT:P1.5 |
| 19836 | W:NT:P1.6 |
| 19383 | E:NT:P1.5, 2 |
| 19504* | X:NT:P1.5, 2 |
| 24196 | X:4:P1.12 |
| 24287 | X:4:P1.16 |
| 23557 | X:NT:P1.5 |

NT: Nontypeable,
NST: Nonsubtypeable
*Strains that were used for capsular polysaccharide purification Purification of the Capsular Polysaccharide from NmX The capsular polysaccharide of serogroup X (cpsX, see FIG. 4A for structural definition) was purified from the NmX strain, 19504 (that gave the highest yield when cultured on GCB medium with Kellogg supplements), by the Cetavlon extraction method as previously described (18). Briefly, bacteria (1 L) at late-logarithmic phase of growth were formaldehyde-inactivated (1% v/v) and then treated with Cetavlon (0.1% w/v) (Sigma Aldrich, France). After centrifugation, the pellet was dissolved in cold aqueous $CaCl_2$ (0.9M). The solubilised materials were cleared by precipitation in 25% aqueous ethanol and the remaining supernatant was precipitated by 80% aqueous ethanol. The pellet was dissolved in phosphate buffer ($Na_2HPO_4$, $NaH_2PO_4$, 0.2 M) and treated with Dnase and Rnase followed by proteinase K treatment (Sigma Aldrich, France) and cold phenol extraction. The extract was extensively dialyzed against distilled water and lyophilized to obtain the crude capsular polysaccharide. Ten mg of the preparation were dissolved in 2 mL of phosphate buffer $K_2HPO_4$, $KH_2PO_4$ (0.05 M), pH 7, and purified by gel filtration on a Biosep-SEC-S3000 column (300×21.2 cm, Phenomenex, France) that was equilibrated with the same buffer. Elution was carried out with the same phosphate buffer at 5 mL/min, and monitored at 214 nm and 280 nm. The void volume fractions containing cpsX in the high molecular-weight range were pooled and dialyzed against distilled water at 4° C., using a dialysis membrane with a cut-off size of 10K-15K, and the residue was lyophilized. The yield was about 20 mg/L of culture. The profile of the purified cpsX was checked by proton nuclear magnetic resonance ($^1H$ NMR) (FIG. 4B) as previously described (19). CpsA, cpsB, cpsC, cpsY and cpsW were similarly purified from five strains of serogroups A, B, C, Y and W (strains 21524, 21721, 22639, 16366 and 19995 respectively, Table 1).

Rabbit Immunization and Purification of Specific Anti-cpsX IgG Antibodies

Two New Zealand White female rabbits (3 kg) were immunised intravenously three times with doses of 1 mL of a suspension of $10^9$ colony forming units (CFU) of freshly heat-inactivated Nmx strain 19504 (30 min at 56° C.), at day 0, 7 and 21. Sera were taken before immunization and at day 28 after the first injection to evaluate the immune response by ELISA (see below). Dot blotting with rabbit sera (1:1000 serum dilution) was performed using Amersham ECL kits (GE Healthcare Life Sciences Velizy-Villacoublay, France) as previously described (20). Rabbit immunisation was performed according to the European Union Directive 2010/63/EU (and its revision 86/609/EEC) on the protection of animals used for scientific purposes. The inventors' laboratory has the administrative authorization for animal experimentation (Permit Number 75-1554) and the protocol was approved by the Institut Pasteur Review Board that is part of in the Regional Committee of Ethics of Animal Experiments of the Paris region (CETEA 2013-0190).

IgG antibody purification was performed by affinity chromatography in two steps. First, the rabbit's sera were passed through a HiTrap Protein G HP column (GE Healthcare, France) and eluted with glycine-HCl 0.1 M pH 2.7. Fractions of 1 mL were recovered in 50 µL of Tris-HCl buffer (1 M, pH 9). Fractions were tested for protein content by measuring their absorbance at 280 nm. Pooled fractions were passed through a cpsX affinity column obtained by chemical coupling of the amine functions of the CarboxyLink resin and the phosphate functions from cpsX, according to manufacturer recommendations (Thermo Scientific, Rockford, Ill. USA). The eluted fractions were tested by ELISA against purified cpsX and whole inactivated NmX bacteria. To do so, ELISA wells were coated overnight with 100 µL of a solution containing 2 µg/mL of purified cpsX or 100 µL of a bacterial suspension of $3.10^8$ bacteria/mL (NmX strain 19504). The purified antibodies (at a 500 µg/ml concentration) were tested against serial dilutions of bacteria from serogroup A, B, C, Y, W and X in a dot blot experiment, and serial dilutions of the antibodies were then tested in ELISA on counterpart coated cps at 2 µg/mL concentration.

Production and Validation of a RDT Against NmX

A one-step vertical flow immune-chromatography dipstick was set up using either only purified cpsX-pAbs (RDT1) or purified anti-cpsX mAbs, with or without cpsX-pAbs (RDT2).

RDT1: Purified cpsX-pAbs that were conjugated to gold particles (British Biocell International, Cardiff, UK) as previously described (21). Unconjugated cpsX-pAbs were used as capture antibodies and goat anti-rabbit IgG (ICN Biomedicals, Aurora, Ohio, United States) were used as control antibodies. Both types of antibodies were sprayed onto nitrocellulose (Schleicher & Schuell Bioscience, Ecquevilly, France) at 2 µg and 1 µg per line centimeter respectively. For the test evaluation, dipsticks were dipped, for a 10-15 min period at room temperature, in 100 µL of PBS containing bacterial suspensions or CSF samples.

RDT2: Purified anti-cpsX mAbs were conjugated to gold particles as described above. Nonconjugated cpsX-mAbs were used as capture antibodies (2 µg per centimeter line), and goat anti-mouse IgG (H+L) (ICN Biomedicals, Aurora, USA) as control antibody (1 µg per line centimeter) after spraying onto nitrocellulose (Schleicher & Schuell Bioscience, Ecquevilly, France). The gold labelled monoclonal antibodies were used at a final OD of 5 in 3% BSA and 10% sucrose containing Phosphate buffer, 50 mM, pH 7.4. For the test evaluation, dipsticks were dipped (for a 10-15 min period at RT) in 150 µL of cpsX containing PBS at the indicated capsule concentration. The dipsticks that use monoclonal IgM as capture antibody and the rabbit polyclonal anti NmX as gold conjugate was performed according to (30).

Data Analysis

Sensitivity (Se), specificity (Sp), positive predictive value (PPV) and negative predictive value (NPV) were calculated using a 2×2 contingency table. The positive likelihood ratios LR ($LR^+$=Se/[1−Sp]) and the negative LR ($LR^-$=[1−Se]/Sp), were also calculated (22). These values give an indication of the likelihood that the sample is positive or negative prior to testing. The diagnostic odds ratio (DOR), defined as the ratio of the odds of positive test results in specimens with NmX on the odds of positive test results in specimens negative for NmX, was calculated as follows DOR=(Se/[1−Se])/([1−Sp/Sp] (23). Finally, the Cohen's kappa (j) statistic was calculated to measure concordance between PCR and RDT (24). K may range from 0 to 1, and a j value higher than 0.8 is thought to reflecting almost perfect.

ELISA

Microtiterplates were coated overnight, at 4° C. with 1 µg/ml capsule in PBS. Following 3 PBST (0.1% Tween 20 containing PBS) washes, antibodies diluted in PBST-G (Gelatin 0.5% containing PBST) at the indicated concentration were added to the wells (1.5 hour at 37° C.). After 3 new PBST washes, a peroxidase labelled anti-mouse IgG(H+L) antibodies were added to the well diluted to 1 µg/ml in PBST-G (1 h at 37° C.). After 3 PBS-T washes the peroxydase substrate solution (OPD, $H_2O_2$) was added to the wells and the OD (optical density) read at 490 nm. For isotype determination antibody binding to cpsX coated plates were revealed by anti-mouse IgG1, IgG2a, IgG3 or IgM peroxidase labelled antibodies and by anti-κ or λ peroxidase labelled antibodies.

Dot-blot

Serial twofold dilutions of inactivated bacteria diluted in PBS were spotted (2 µl) on supported nitrocellulosis. After nitrocellulosis drying, the antibodies were added onto the membrane for an overnight incubation at 4° C. Three PBST washes (15 min each) were then performed and the peroxydase labelled antibodies was added as described in the ELISA protocol. Peroxydase activity product was read with ECL substrate.

Antibody Sequencing

```
Primers specific for IgM H chain:
                                       (SEQ ID No 10)
ATGCAGACTAGTGTTTTTGCCTCCGTAGTGG
and (SEQ ID No 11)
CCTAGGGGAGGTGCAGCTTGAGGAGTCAGGACC
and
```

```
for K light chain:
                                       (SEQ ID No 12)
TTCTAGACTAACACTCATTCCTGTTGAA
and (SEQ ID No 13)
AAGATCTGAGCTCGTGATGACCCAGACTCCA
``` were used to amplify by PCR the CDR coding regions of the antibodies. The template was the c-DNAs obtained after RT PCR of antibody producing hybridoma mRNA. The same primers were used to sequence the PCR products obtained and the forward and reverse sequences were compared.

Immunisation

BALB/c mice were immunized in Institut Pasteur according to the classical protocols. Four BALB/c mice (female 8 weeks) were immunized subcutaneously with 5 doses of 0.2 ml each of a suspension of 5×106 CFU of freshly heat-inactivated NmX strain 19504 (inactivation by heating 30 min at 56° C.) on days 0, 7, 14, 21 and 42. Serum samples were taken before immunization and one week after the fifth injection to evaluate the immune response by enzyme-linked immunosorbent assay (ELISA) and dot blotting.

Fusion

Fusion was performed according to (28) (Kohler, G. and Milstein, C). Due to the difficulty to obtain active antibodies starting from hybridoma culture medium, the inventors raised ascitis, by using IFA (Incomplete Freund's Adjuvant) as activator. Antibodies were purified in a pH independent procedure using water purification (29).

Example 2: Characterization of Rabbit Anti-meningococcal Serogroup X Rabbit Serum Following the three dose-immunization regimen with whole NmX bacteria, the rabbit sera were tested in dot blot analysis against spotted bacteria. While no bacteria detection was obtained with control pre-immune sera, a strong detection was obtained with the sera from immunized rabbits (FIG. 1). Sera from the two responding rabbits were pooled and anti-cpsX-specific IgG were purified by affinity chromatography on a NmX cps activated column. Dot plot analysis of the purified IgG response against decreasing numbers of bacteria (from $5×10^5$ to $5×10^3$ cells per spot) from serogroups A, B, C, Y, W and X showed that antibodies only recognized serogroup X strain (FIG. 2A). The absence of recognition of the other serogroups (A, B, C, Y and W) was further confirmed independently by ELISA analysis of the antibody response against coated (1 µg/mL) purified cps corresponding to the six serogroups (FIG. 2B).

A dipstick rapid diagnostic test for NmX was produced (see Material and Methods, RDT1), and its detection limits were established. For the purified cpsX, this limit was 1 ng/mL (FIG. 2C) and was $10^5$ CFU/mL for NmX bacteria (strain 19504). The cut-off analysis was repeated 3 times with identical findings that were not affected by dipstick storage for 3 weeks at 25° C. The inventors also tested the RDT on a collection of bacterial suspension (Table 1) at $10^6$ CFU/mL. Only the serogroup X isolates were detectable.

The detection limit of 1 ng CpsX/ml is similar to that of ELISA assays and lower than that of latex agglutination assays (10-100 ng CpsX/ml), explaining the higher specificities and sensitivities of RDTs compared with the agglutination kit.

Use of the NmX Dipsticks (RDT1) on Clinical Samples

The NmX dipstick RDT1 was tested on a panel of 369 CSF selected from historical collections kept in National Reference Centre/Laboratory from four different countries, differing in terms of meningitis incidence (Cameroon, Côte d'Ivoire, France and Niger). Noticeably, three out of the four laboratories are located in countries within the meningitis belt. The CSF samples corresponded to suspected cases of acute bacterial meningitis. They were characterized by PCR for etiological diagnosis (Table 2). Culture results were only available for 26 samples (8 samples positive for *S. pneumoniae*, 4 positive for *N. meningitidis* (2 serogroup B and 2 serogroup W), 1 positive for *H. influenzae*, 1 positive for *S. agalactiae* and 12 CSF samples were sterile by culture).

Among these isolates, 52% (n=191) were positive for Nm, 8% (n=28) were positive for other bacterial species, namely *S. pneumoniae*, *H. influenzae* and *S. agalactiae*, and 40% (n=150) were negative by PCR for these species. Among the Nm positive CSF, the six meningococcal capsular groups involved in invasive meningococcal infections were represented: group A (n=27), group B (n=8), group C (n=7), group Y (n=2), group W (n=38) and group X (n=92). In addition, 17 CSF samples were positive for Nm by PCR although they were negative for groups A, B, C, Y, W and X. All samples that were negative for NmX by PCR were also negative for this group by the new NmX-specific RDT. Among the 92 CSF positive for NmX by PCR, 86 were also positive by RDT. All the 26 CSF samples with culture data were tested negative by NmX-specific RDT.

This validation under laboratory conditions took place during the epidemic season in the three laboratories located in countries of the meningitis belt. Therefore, the inventors took advantage of the epidemic season and tested the new NmX-specific RDT on all 153 CSF samples that were received in the three laboratories in Cameroon, Côte d'Ivoire and Niger. No NmX was detected by PCR or by RDT in any of the samples. In contrast, several samples were positive by PCR for *S. pneumoniae* (14%), NmW (7%) and *H. influenzae* (3%).

of the RDT obtained for the documented 369 CSF samples are summarized in Table 3. The specificity of RDT for CSF infected by NmX was 100%, while the sensitivity reached 94%. Calculating the positive likelihood $LR^+$ and DOR was not feasible due to a Sp value of 100%. $LR^+$ and DOR values were therefore calculated using a value for the specificity that corresponded to the lower 95% confidence interval for specificity (0.99) (Table 3).

TABLE 3

Performance of the RDT (RDT1) for NmX

| Test parameter | Value | 95% confidence interval |
|---|---|---|
| Sensitivity (Se) | 0.94 | 0.86 to 0.98 |
| Specificity (Sp) | 1 | 0.99 to 1 |
| Positive Likelihood ratio ($Lh^+$)* | 94 | 32 to 8252 |
| Negative Likelihood ratio ($LH^-$) | 0.07 | 0.03 to 0.15 |
| Positive predictive value (PPV) | 1 | 0.96 to 1 |
| Negative predictive value (NPV) | 0.98 | 0.95 to 0.99 |
| Diagnostic odd ratio (DOR)* | 1567 | 379 to 118420 |

Dividing by zero; the values of $LH^+$ and DOR were calculated using a value for specificity that corresponded to the lower 95% confidence interval (0.99).

The prevalence of NmX among the 369 tested CSF was 25%. Therefore, the NPV and PPV are given in Table 3 under this prevalence value. However, the tested samples were selected from the collections of the participating laboratories and may not reflect the real prevalence of the disease. Moreover, the frequency of NmX meningitis may also vary across time and countries within the meningitis belt and elsewhere. We therefore calculated the negative and positive predictive values (NPV and PPV) according to a prevalence varying from 0 to 100%, using the Se and Sp obtained from the CSF samples in this study (FIG. 3).

TABLE 2

Results of CSF samples obtained by PCR and by RDT

| | Geographical origins | | | | | RDT | |
|---|---|---|---|---|---|---|---|
| PCR | IP Paris | CERMES | CP Garoua | IP Côte d'Ivoire | Total | $NmX^+$ | $NmX^-$ |
| NmA | 6 | 15 | 6 | 0 | 27 | 0 | 27 |
| NmB | 6 | 0 | 0 | 2 | 8 | 0 | 8 |
| NmC | 7 | 0 | 0 | 0 | 7 | 0 | 7 |
| NmY | 2 | 0 | 0 | 0 | 2 | 0 | 2 |
| NmW | 6 | 10 | 4 | 18 | 38 | 0 | 38 |
| NmX | 7 | 80 | 5 | 0 | 92 | 86 | 6 |
| Nm NG | 0 | 0 | 16 | 1 | 17 | 0 | 17 |
| *S. pneumoniae* | 0 | 0 | 10 | 13 | 23 | 0 | 23 |
| *H. influenzae* | 0 | 0 | 1 | 3 | 4 | 0 | 4 |
| *S. agalactiae* | 1 | 0 | 0 | 0 | 1 | 0 | 1 |
| Negative* | 10 | 0 | 77 | 63 | 150 | 0 | 150 |
| Total | 45 | 105 | 119 | 100 | 369 | 86 | 283 |

*PCR Negative for *N. meningitidis*, *S. pneumoniae* and *H. influenzae*
CSF: cerebrospinal fluid;
RDT: Rapid Diagnostic test;
IP, Institut Pasteur;
CP: centre Pasteur;
Nm: *Neisseria meningitidis*;
NG: non groupeable Performance of the NmX-specific RDT1: Sensitivity, Specificity, Likelihood Ratios, and Predictive Values RDT data showed a good correlation with PCR data, indicating a Kappa correlation coefficient of 98%. The sensitivity, specificity and 95% CI (confident interval) data Discussion Reliable tests for the identification of cases of meningococcal meningitis and serogroup-determination are crucial to ensure proper individual (case-by-case) as well as collective management of cases and epidemiological surveillance. Culturing *N. meningitidis* may frequently fail due to early antibiotic treatment and fragility of this bacterial species (25). During the last two decades, PCR-based non-culture methods have been developed, enabling a significant improvement of the management and surveillance of bacterial meningitis (26). PCR-based methods require specific laboratory equipment and trained staff and can not be used as a bedside method (i.e. for physicians to make a decision on individual treatment). Nevertheless, the PCR technology was implemented in several reference laboratories located in countries within the African meningitis belt (26). However, PCR may not be sufficiently set to ensure country-wide surveillance, especially in populations leaving in remote areas. Other tests, such as the currently available latex agglutination kits, require trained staff and an unbroken cold chain for storage and distribution of the kits. The recent implementation of RDT for meningococci of serogroups A, C, Y and W was a major breakthrough for individual diagnosis and for surveillance of meningococcal diseases in the African meningitis belt (12). These tests are stable at temperature up to 45° C. at least. They are easy to use and to interpret in the absence of extensive training, and therefore are adapted for bedside use. The emergence of meningococcal isolates of serogroup X urged the development of a RDT test for this serogroup to complete the current RDT tools. The inventors first analyzed the inherent quality of such a serogroup X specific test. The specificity and sensitivity parameters were evaluated under laboratory conditions using a selected panel of relevant CSF samples. The good quality of the new RDT was reflected by its high sensitivity and specificity for NmX with a very high likelihood ratio for positive test (Table 3). The inventors also evaluated its usefulness that depends not only on the quality of the test but also on the prevalence of the NmX meningitis in the tested population. The prevalence of NmX within the panel of CSF samples that was used to evaluate the RDT specificity and sensitivity was 25.7%. It may not properly reflect the real prevalence of NmX in areas at risk. Usefulness is usually evaluated using two parameters, the PPV and NPV. When NmX prevalence was forced to vary between 0 and 100%, the PPV remained stable at 1 indicating that the test remained highly proficient in ruling-in a case. Moreover, the NPV retained high values when the prevalence of NmX was very low. In addition, the test remained proficient (NPV of 0.95 or higher) if this prevalence increased to 50%. These considerations seem realistic and reflect the current epidemiological situation in the meningitis belt after the introduction of MenAfriVac™ that was associated with significant decrease of NmA (9). Indeed, the small scale prospective use of the new RDT in the three centres located in this area (Abidjan, Garoua and Niamey), which is disclosed herein, suggests, on the basis of the sensitivities of RDT and PCR (that are less than 100%) that NmX may be present albeit not as a dominating pathogen. In contrast, NmW was the most frequently isolated Nm species, while most cases were associated to *S. pneumoniae*. However, a large-scale multi-site prospective study comparing PCR and all the available RDT (A, C, Y, W, Y and X) is warranted in the future. The new RDT described here will be crucial in vaccination decision making to implement large scale vaccination with the available broad serogroup coverage vaccine that can target NmX (5) or with NmX-specific vaccines under development (14).

Example 3: Development of a Monoclonal Antibody

In view of the performance and validation of RDT1 as described above, the inventors then have looked for improved reproducibility of RDT1, inter alia by using a monoclonal antibody. In this respect, whole inactivated NmX bacteria were used to immunize mice from the BALB/c strain. Hybridomas were obtained by fusing cells extracted from spleen of immunized mice, with plasmacytoma P3U1. Two IgM,κ monoclonal antibodies, named K1-5 and K7-1 were obtained in one fusion after screening on cps X coated ELISA plates. The hybridoma cell cultures producing these antibodies were deposited at the CNCM, (Collection nationale de cultures de micro-organismes (CNCM) Institut Pasteur; 25-28, rue du Docteur Roux; 75724 Paris Cedex 15 FRANCE), on 21 May 2015, under the accession number I-4983 for K1-5 and I-4984 for K7-1.

Due to their instability upon purification from hybridoma culture medium, the two IgMs were purified from ascitis using water purification. They were able to detect coated cpsX capsules down to few ng/ml of antibody concentration (FIG. 5).

Several immunological tests were performed demonstrating that the antibodies were specific to the capsule of the X serogroup, that they did not show detectable recognition for other capsular polysaccharides (FIG. 6) and that they were able to bind specifically *Neisseria meningitidis* NmX bacteria but not non-NmX meningococcal isolates (FIG. 7). The dot blot gave similar results when using the K7-1 antibody (not shown).

Sequencing of the two antibody's CDR demonstrated that they unexpectedly display the same CDR sequences (FIG. 8), for the 6 CDRs. The variable regions of both antibodies are also in their entirety almost identical.

Immunochromatography RDT2 (rapid diagnostic test) were set up, first using IgM antibodies as capture antibodies and the gold labeled rabbit polyclonal antibodies, as described in example 2, to detect the serogroup X capsule. The detection sensitivity of these dipsticks was of 2.5 ng/ml of purified cpsX capsule (FIG. 9) whatever the IgM used as capture antibody, i.e. K1-5 or K7-1. This demonstrates that the IgM could be used as capture antibody and could replace the polyclonal antibody used in example 2, in the X specific detection dipstick. Trials using the monoclonal IgM antibodies both as capture antibodies and as gold conjugated antibodies lead to lower detection sensitivities (FIG. 10) whatever the capture/conjugated antibody couple used. This lower sensitivity is however likely to be at least partially due to non-optimal labeling with the gold particles; such that improvement is expected by optimization of at least this step.

These results on RDT2 validate the use of monoclonal antibodies in RDT, as a substitute of polyclonal antibodies, either as detection antibodies, or as capture antibodies, or preferably as both detection and capture antibodies. This is the first RDT designed with IgM monoclonal antibodies.

REFERENCES

1. Rosenstein N E, Perkins B A, Stephens D S, Popovic T, Hughes J M. 2001. Meningococcal disease. N Engl J Med. 344: 1378-1388.
2. Harrison L H, et al. 2011. Vaccine. 29: 3363-3371.
3. Harrison L H, Trotter C L, Ramsay M E. 2009. Vaccine. 27 Suppl 2: B51-63.
4. O'Ryan M, Stoddard J, Toneatto D, Wassil J, Dull P M. 2014. Drugs. 74: 15-30.
5. Hong E, Giuliani M M, Deghmane A E, Comanducci M, Brunelli B, Dull P, Pizza M, Taha M K. 2013. Vaccine. 31: 1113-1116.

6. Frasch C E, Preziosi M P, LaForce F M. 2012. Development of a group A meningococcal conjugate vaccine, MenAfriVac™. Hum Vaccin Immunother. 8: 715-724.
7. Boisier P, Nicolas P, Djibo S, Taha M K, Jeanne I, Mainassara H B, Tenebray B, Kairo K K, Giorgini D, Chanteau S. 2007. Clin Infect Dis. 44: 657-663.
8. Taha M K, Parent Du Chatelet I, Schlumberger M, Sanou I, Djibo S, de Chabalier F, Alonso J M. 2002. J Clin Microbiol. 40: 1083-1084.
9. Collard J M, Issaka B, Zaneidou M, Hugonnet S, Nicolas P, Taha M K, Greenwood B, Jusot J F. 2013. BMC Infect Dis. 13: 576.
10. Terrade A, Collard J M, Nato F, Taha M K. 2013. Laboratory evaluation of a rapid diagnostic test for *Neisseria meningitidis* serogroup A. Trans R Soc Trop Med Hyg.
11. Chanteau S, Sidikou F, Djibo S, Moussa A, Mindadou H, Boisier P. 2006. Trans R Soc Trop Med Hyg. 100: 677-680.
12. Chanteau S, Dartevelle S, Mahamane A E, Djibo S, Boisier P, Nato F. 2006. New rapid diagnostic tests for *Neisseria meningitidis* serogroups A, W135, C, and Y. PLoS Med. 3: e337.
13. European Centre for Disease Prevention and Control. 2013. Annual Epidemiological Report 2012. Reporting on 2010 surveillance data and 2011 epidemic intelligence data. Stockholm: ECDC.
14. Micoli F, Romano M R, Tontini M, Cappelletti E, Gavini M, Proietti D, Rondini S, Swennen E, Santini L, Filippini S, Balocchi C, Adamo R, Pluschke G, Norheim G, Pollard A, Saul A, Rappuoli R, MacLennan C A, Berti F, Costantino P. 2013. Proc Natl Acad Sci USA. 110: 19077-19082.
15. Kellogg D S, Jr., Peacock W L, Jr., Deacon W E, Brown L, Pirkle D I. 1963. J Bacteriol. 85: 1274-1279.
16. Ballard T L, Roe M H, Wheeler R C, Todd J K, Glode M P. 1987. Pediatr Infect Dis J. 6: 630-634.
17. Abdillahi H, Poolman J T. 1988. *Neisseria meningitidis* group B serosubtyping using monoclonal antibodies in whole-cell ELISA. Microb Pathog. 4: 27-32.
18. Nato F, Mazie J C, Fournier J M, Slizewicz B, Sagot N, Guibourdenche M, Postic D, Riou J Y. 1991. J Clin Microbiol. 29: 1447-1452.
19. Xie O, Bolgiano B, Gao F, Lockyer K, Swann C, Jones C, Delrieu I, Njanpop-Lafourcade B M, Tamekloe T A, Pollard A J, Norheim G. 2012. Vaccine. 30: 5812-5823.
20. Taha M K, Giorgini D. 1995. Phosphorylation and functional analysis of PilA, a protein involved in the transcriptional regulation of the pilin gene in *Neisseria gonorrhoeae*. Mol Microbiol. 15: 667-677.
21. Chanteau S, Rahalison L, Ralafiarisoa L, Foulon J, Ratsitorahina M, Ratsifasoamanana L, Carniel E, Nato F. 2003. Development and testing of a rapid diagnostic test for bubonic and pneumonic plague. Lancet. 361: 211-216.
22. Jaeschke R, Guyatt G H, Sackett D L. 1994. Users' guides to the medical literature. III. How to use an article about a diagnostic test. B. What are the results and will they help me in caring for my patients? The Evidence-Based Medicine Working Group. JAMA. 271: 703-707.
23. Glas A S, Lijmer J G, Prins M H, Bonsel G J, Bossuyt P M. 2003. The diagnostic odds ratio: a single indicator of test performance. J Clin Epidemiol. 56: 1129-1135.
24. Cohen J. 1960. A coefficient of agreement for nominal scales. Edu Psychol Measur. 20: 37-46.
25. Cartwright K A, Reilly S, White D, Stuart J. 1992. Early treatment with parenteral penicillin in meningococcal disease. Bmj. 305: 143-147.
26. Parent du Chatelet I, Traore Y, Gessner B D, Antignac A, Naccro B, Njanpop-Lafourcade B M, Ouedraogo M S, Tiendrebeogo S R, Varon E, Taha M K. 2005. Clin Infect Dis. 40: 17-25.
27. Rissin, D M., et al. 2010. Single-molecule enzyme-linked immunosorbent assay detects serum proteins at subfemtomolat concentrations. Nat. Biotechnol. 28: 595-600.
28. Kohler, G. and Milstein, C. 1975. Nature, 255: 495-497.
29. Garcia-Gonzales M. et al. 1988. J. Immunol. Methods, 111, 17-23.
30. Agnememel et al. 2014. J Clin Microbiol., 53, 449-54.
31. Reyes et al. 2014. Biologicals, 42(6), 312-5.
32. Scaviner, D., Barbié, V., Ruiz, M. and Lefranc, M.-P. 1999. Exp. Clin. Immunogenet., 16, 234-240.
33. Kaas, Q. and Lefranc, M.-P. 2007. Current Bioinformatics, 2, 21-30.

The invention claimed is:

1. A monoclonal antibody or an antigen-binding portion thereof, that binds specifically to the capsular polysaccharides of *Neisseria meningitidis* serogroup X (NmX), wherein said antibody or fragment thereof comprises at least one heavy chain variable region (VH) comprising a heavy chain CDR1 set forth in SEQ ID NO: 1, a heavy chain CDR2 set forth in SEQ ID NO: 2 and a heavy chain CDR3 set forth in SEQ ID NO: 3, and an associated light chain variable region ($V_L$) comprising a light chain CDR1 set forth in SEQ ID NO: 4, a light chain CDR2 set forth in SEQ ID NO: 5, and a light chain CDR3 set forth in SEQ ID NO: 6.

2. The monoclonal antibody according to claim 1, wherein said antibody is an immunoglobulin M (IgM) or immunoglobulin G (IgG).

3. The monoclonal antibody according to claim 1, wherein said antibody comprises a heavy chain variable region having an amino acid sequence set forth in SEQ ID NO: 7 or in SEQ ID NO: 8.

4. A monoclonal antibody according to claim 1, wherein said antibody comprises a light chain variable region having an amino acid sequence of set forth in SEQ ID NO: 9.

5. The monoclonal antibody according to claim 1, wherein said antibody is obtainable from the murine hybridoma cell culture K1-5 deposited at the CNCM on 21 May 2015 under the accession number I-4983, or from the murine hybridoma cell culture K7-1 deposited at the CNCM on 21 May 2015 under the accession number I-4984.

6. The monoclonal antibody according to claim 1, which does not cross-react with *Neisseria meningitidis* serogroups A, B, C, Y, W, Z, E, H, I, K and L.

7. A diagnostic agent characterized in that it comprises a monoclonal antibody as defined in claim 1, linked directly or indirectly, covalently or non-covalently to a detection label.

8. A method for detecting in vitro or ex vivo *Neisseria meningitidis* serogroup X in a biological fluid, said method comprising
 a. contacting in vitro said fluid with a monoclonal antibody according to claim 1, and
 b. determining the presence or absence of capsular polysaccharides of *Neisseria meningitidis* serogroup X in said fluid, wherein the presence of capsular polysaccharides of *Neisseria meningitidis* serogroup X is indicative of the presence of *Neisseria meningitidis* serogroup X in the biological fluid.

9. An in vitro method for diagnosing a *Neisseria meningitidis* serogroup X infection in a subject, comprising carrying out the method according to claim 8 on a biological fluid sample from said subject, wherein the presence of capsular polysaccharides of *Neisseria meningitidis* serogroup X in said fluid is indicative of *Neisseria meningitidis* serogroup X infection.

10. A diagnostic kit for detecting *Neisseria meningitidis* serogroup X, comprising at least one monoclonal antibody according to claim 1, and means for detecting the production of an immune complex between said antibody and capsular polysaccharides of *Neisseria meningitidis* serogroup X.

11. A dipstick diagnostic test for NmX, comprising a membrane, wherein said membrane comprises:
 a. a first zone comprising antibodies, specific for the capsular polysaccharides of NmX, conjugated to a detection label;
 b. a control zone comprising an immobilized control polypeptide; and
 c. a capture zone comprising immobilized antibodies specific for the capsular polysaccharides of NmX, as capture antibodies;
 wherein the antibodies conjugated to a detection label of the first zone, or the capture antibodies of the capture zone, or both the antibodies of the first zone and of the capture zone, are monoclonal antibodies according to claim 1.

12. The dipstick diagnostic test according to claim 11, wherein either the antibodies conjugated to a detection label or the capture antibodies of the capture zone, are polyclonal antibodies obtainable by immunization of a rabbit with whole inactivated *Neisseria meningitidis* serogroup X, followed by purification of the rabbit serum by affinity chromatography with purified *Neisseria meningitidis* serogroup X capsular polysaccharides.

13. The dipstick diagnostic test according to claim 11, wherein the antibodies of the capture zone are polyclonal antibodies obtainable by immunization of a rabbit with whole inactivated *Neisseria meningitidis* serogroup X, followed by purification of the rabbit serum by affinity chromatography with purified *Neisseria meningitidis* serogroup X capsular polysaccharides, wherein the antibodies of the first zone are mouse monoclonal antibodies that comprise at least one heavy chain variable region (VH) comprising a heavy chain CDR1 set forth in SEQ ID NO: 1, a heavy chain CDR2 set forth in SEQ ID NO: 2 and a heavy chain CDR3 set forth in SEQ ID NO: 3, and an associated light chain variable region ($V_L$) comprising a light chain CDR1 set forth in SEQ ID NO: 4, a light chain CDR2 set forth in SEQ ID NO: 5, and a light chain CDR3 set forth in SEQ ID NO: 6, and wherein the immobilized control polypeptides are anti-mouse antibodies that bind to the mouse monoclonal antibodies of the first zone.

14. A method for detecting in vitro or ex vivo *Neisseria meningitidis* serogroup X in a biological fluid, said method comprising
   a. contacting in vitro said fluid with a diagnostic agent according to claim 7, and
   b. determining the presence or absence of capsular polysaccharides of *Neisseria meningitidis* serogroup X in said fluid, wherein the presence of capsular polysaccharides of *Neisseria meningitidis* serogroup X is indicative of the presence of *Neisseria meningitidis* serogroup X in the biological fluid.

15. An in vitro method for diagnosing a *Neisseria meningitidis* serogroup X infection in a subject, comprising carrying out the method according to claim 14 on a biological fluid sample from said subject, wherein the presence of capsular polysaccharides of *Neisseria meningitidis* serogroup X in said fluid is indicative of *Neisseria meningitidis* serogroup X infection.

16. A diagnostic kit for detecting *Neisseria meningitidis* serogroup X, comprising a diagnostic agent according to claim 7, and means for detecting the production of an immune complex between said antibody and capsular polysaccharides of *Neisseria meningitidis* serogroup X.

17. The dipstick diagnostic test according to claim 11, wherein the antibodies of the first zone are polyclonal antibodies obtainable by immunization of a rabbit with whole inactivated *Neisseria meningitidis* serogroup X, followed by purification of the rabbit serum by affinity chromatography with purified *Neisseria meningitidis* serogroup X capsular polysaccharides, and wherein the antibodies of the capture zone are mouse monoclonal antibodies that comprise at least one heavy chain variable region (VH) comprising a heavy chain CDR1 set forth in SEQ ID NO: 1, a heavy chain CDR2 set forth in SEQ ID NO: 2 and a heavy chain CDR3 set forth in SEQ ID NO: 3, and an associated light chain variable region ($V_L$) comprising a light chain CDR1 set forth in SEQ ID NO: 4, a light chain CDR2 set forth in SEQ ID NO: 5, and a light chain CDR3 set forth in SEQ ID NO: 6.

* * * * *

SEQUENCE LISTING

```
<160> NUMBER OF SEQ ID NOS: 13

<210> SEQ ID NO 1
<211> LENGTH: 7
<212> TYPE: PRT
<213> ORGANISM: Mus musculus

<400> SEQUENCE: 1

Gly Phe Ser Leu Thr Ser Tyr
1               5

<210> SEQ ID NO 2
<211> LENGTH: 6
<212> TYPE: PRT
<213> ORGANISM: Mus musculus

<400> SEQUENCE: 2

Ile Trp Ala Gly Gly Ser
1               5

<210> SEQ ID NO 3
```

```
<211> LENGTH: 11
<212> TYPE: PRT
<213> ORGANISM: Mus musculus

<400> SEQUENCE: 3

Ala Arg Ala Leu Leu Arg Gly Ala Met Asp Tyr
1               5                   10

<210> SEQ ID NO 4
<211> LENGTH: 11
<212> TYPE: PRT
<213> ORGANISM: Mus musculus

<400> SEQUENCE: 4

Gln Ser Leu Val His Ser Asn Gly Asn Thr Tyr
1               5                   10

<210> SEQ ID NO 5
<211> LENGTH: 3
<212> TYPE: PRT
<213> ORGANISM: Mus musculus

<400> SEQUENCE: 5

Lys Val Ser
1

<210> SEQ ID NO 6
<211> LENGTH: 9
<212> TYPE: PRT
<213> ORGANISM: Mus musculus

<400> SEQUENCE: 6

Ser Gln Ser Thr His Val Pro Pro Thr
1               5

<210> SEQ ID NO 7
<211> LENGTH: 120
<212> TYPE: PRT
<213> ORGANISM: Mus musculus

<400> SEQUENCE: 7

Ile Gly Leu Val Ala Pro Ser Gln Ser Met Tyr Ile Thr Cys Thr Val
1               5                   10                  15

Ser Gly Phe Ser Leu Thr Ser Tyr Gly Val His Trp Val Arg Gln Pro
            20                  25                  30

Pro Gly Lys Gly Leu Glu Trp Leu Gly Val Ile Trp Ala Gly Gly Ser
        35                  40                  45

Thr Asn Tyr Asn Ser Ala Leu Met Ser Arg Leu Ser Ile Ser Lys Asp
    50                  55                  60

Asn Ser Lys Ser Gln Val Phe Leu Lys Met Asn Ser Leu Gln Thr Asp
65                  70                  75                  80

Asp Thr Ala Met Tyr Tyr Cys Ala Arg Ala Leu Leu Arg Gly Ala Met
                85                  90                  95

Asp Tyr Trp Gly Gln Gly Thr Ser Val Thr Val Ser Ser Glu Ser Gln
            100                 105                 110

Ser Phe Pro Asn Val Phe Pro Leu
        115                 120

<210> SEQ ID NO 8
<211> LENGTH: 120
<212> TYPE: PRT
<213> ORGANISM: Mus musculus
```

<400> SEQUENCE: 8

```
Ile Gly Leu Val Ala Pro Ser Gln Ser Leu Ser Ile Thr Cys Thr Val
1               5                   10                  15
Ser Gly Phe Ser Leu Thr Ser Tyr Gly Val His Trp Val Arg Gln Pro
            20                  25                  30
Pro Gly Lys Gly Leu Glu Trp Leu Gly Val Ile Trp Ala Gly Gly Ser
        35                  40                  45
Thr Asn Tyr Asn Ser Ala Leu Met Ser Arg Leu Ser Ile Ser Lys Asp
50                  55                  60
Asn Ser Lys Ser Gln Val Phe Leu Lys Met Asn Ser Leu Gln Thr Asp
65                  70                  75                  80
Asp Thr Ala Met Tyr Tyr Cys Ala Arg Ala Leu Leu Arg Gly Ala Met
                85                  90                  95
Asp Tyr Trp Gly Gln Gly Thr Ser Val Thr Val Ser Ser Glu Ser Gln
            100                 105                 110
Ser Phe Pro Asn Val Phe Pro Leu
        115                 120
```

<210> SEQ ID NO 9
<211> LENGTH: 120
<212> TYPE: PRT
<213> ORGANISM: Mus musculus

<400> SEQUENCE: 9

```
Leu Ser Leu Pro Val Ser Leu Gly Asp Gln Ala Ser Ile Ser Cys Arg
1               5                   10                  15
Ser Ser Gln Ser Leu Val His Ser Asn Gly Asn Thr Tyr Leu His Trp
            20                  25                  30
Tyr Leu Gln Lys Pro Gly Gln Ser Pro Lys Leu Leu Ile Tyr Lys Val
        35                  40                  45
Ser Asn Arg Phe Ser Gly Val Pro Asp Arg Phe Ser Gly Ser Gly Ser
50                  55                  60
Gly Thr Asp Phe Thr Leu Lys Ile Ser Arg Val Glu Ala Glu Asp Leu
65                  70                  75                  80
Gly Val Tyr Phe Cys Ser Gln Ser Thr His Val Pro Pro Thr Phe Gly
                85                  90                  95
Gly Gly Thr Lys Leu Glu Ile Lys Arg Ala Asp Ala Ala Pro Thr Val
            100                 105                 110
Ser Ile Phe Pro Pro Ser Ser Glu
        115                 120
```

<210> SEQ ID NO 10
<211> LENGTH: 31
<212> TYPE: DNA
<213> ORGANISM: artificial
<220> FEATURE:
<223> OTHER INFORMATION: primer for IgM Heavy chain

<400> SEQUENCE: 10
atgcagacta gtgtttttgc ctccgtagtg g       31

<210> SEQ ID NO 11
<211> LENGTH: 33
<212> TYPE: DNA
<213> ORGANISM: artificial
<220> FEATURE:
<223> OTHER INFORMATION: primer for IgM Heavy chain

```
<400> SEQUENCE: 11
cctaggggag gtgcagcttg aggagtcagg acc                         33

<210> SEQ ID NO 12
<211> LENGTH: 28
<212> TYPE: DNA
<213> ORGANISM: artificial
<220> FEATURE:
<223> OTHER INFORMATION: primer for IgM light chain

<400> SEQUENCE: 12
ttctagacta acactcattc ctgttgaa                               28

<210> SEQ ID NO 13
<211> LENGTH: 31
<212> TYPE: DNA
<213> ORGANISM: artificial
<220> FEATURE:
<223> OTHER INFORMATION: primer for IgM Light chain

<400> SEQUENCE: 13
aagatctgag ctcgtgatga cccagactcc a                           31
```